(12) United States Patent
Grauert et al.

(10) Patent No.: US 9,440,960 B2
(45) Date of Patent: Sep. 13, 2016

(54) SUBSTITUTED OXETANES AND THEIR USE AS INHIBITORS OF CATHEPSIN C

(71) Applicant: Boehringer Ingelheim International GmbH, Ingelheim am Rhein (DE)

(72) Inventors: Matthias Grauert, Biberach an der Riss (DE); Ralf Anderskewitz, Laupheim (DE); Achim Bixenmann, Uttenweiler (DE); Marc Grundl, Biberach an der Riss (DE); Peter Wilhelm Haebel, Mittelbiberach (DE); Alexander Pautsch, Biberach an der Riss (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 14/814,759

(22) Filed: Jul. 31, 2015

(65) Prior Publication Data
US 2016/0031861 A1 Feb. 4, 2016

(30) Foreign Application Priority Data
Aug. 1, 2014 (EP) ..................................... 14179458

(51) Int. Cl.
| | | |
|---|---|---|
| C07D 487/10 | (2006.01) | |
| C07D 405/14 | (2006.01) | |
| C07D 471/08 | (2006.01) | |
| C07D 405/12 | (2006.01) | |
| A61K 31/496 | (2006.01) | |
| A61K 45/06 | (2006.01) | |
| C07D 487/08 | (2006.01) | |
| A61K 31/4995 | (2006.01) | |
| A61K 31/403 | (2006.01) | |
| A61K 31/4439 | (2006.01) | |
| C07D 487/04 | (2006.01) | |
| A61K 31/407 | (2006.01) | |
| A61K 31/454 | (2006.01) | |
| A61K 31/439 | (2006.01) | |

(52) U.S. Cl.
CPC ........... *C07D 405/12* (2013.01); *A61K 31/403* (2013.01); *A61K 31/407* (2013.01); *A61K 31/439* (2013.01); *A61K 31/4439* (2013.01); *A61K 31/454* (2013.01); *A61K 31/496* (2013.01); *A61K 31/4995* (2013.01); *A61K 45/06* (2013.01); *C07D 405/14* (2013.01); *C07D 471/08* (2013.01); *C07D 487/04* (2013.01); *C07D 487/08* (2013.01); *C07D 487/10* (2013.01)

(58) Field of Classification Search
CPC C07D 405/12; C07D 487/08; C07D 487/10; C07D 405/14; C07D 487/04; C07D 471/08
USPC ................................................ 546/152, 125
See application file for complete search history.

(56) References Cited

U.S. PATENT DOCUMENTS

| | | |
|---|---|---|
| 4,125,727 A | 11/1978 | Los |
| 7,012,075 B2 | 3/2006 | Prasit et al. |
| 7,902,181 B2 | 3/2011 | Furber et al. |
| 8,987,249 B2 | 3/2015 | Anderskewitz et al. |
| 2006/0223846 A1 | 10/2006 | Dyatkin et al. |
| 2013/0172327 A1 | 7/2013 | Grundl et al. |

FOREIGN PATENT DOCUMENTS

| | | |
|---|---|---|
| WO | 0202556 A2 | 1/2002 |
| WO | 2004110988 A1 | 12/2004 |
| WO | 2005042533 A2 | 5/2005 |
| WO | 2009047829 A1 | 4/2009 |
| WO | 2009074829 A1 | 6/2009 |
| WO | 2010128324 A1 | 11/2010 |
| WO | 2010142985 A1 | 12/2010 |
| WO | 2012119941 A1 | 9/2012 |
| WO | 2013041497 A1 | 3/2013 |

OTHER PUBLICATIONS

Abstract in English for WO 2009/047829, publication date Apr. 16, 2009.
Adkison, A.M. et al., "Dipeptidyl peptidase I activates neutrophil-derived serine proteases and regulates the development of acute experimental arthritis." The Journal of Clinical Investigation, 2002, vol. 109, No. 3, pp. 363-371.
Akk, A.M. et al., "Dipeptidyl Peptidase I-Dependent Neutrophil Recruitment Modulates the Inflammatory Response to Sendai Virus Infection." The Journal of Immunology, 2008, vol. 180, pp. 3535-3542.
Bondebjerg, J. et al., "Dipeptidyl nitriles as human dipeptidyl peptidase I inhibitors." Bioorganic & Medicinal Chemistry Letters, 2006, vol. 16, No. 13, pp. 3614-3617.

(Continued)

*Primary Examiner* — Jennifer M Kim
(74) *Attorney, Agent, or Firm* — Michael P. Morris; Usha R. Patel

(57) ABSTRACT

This invention relates to a compound of formula I

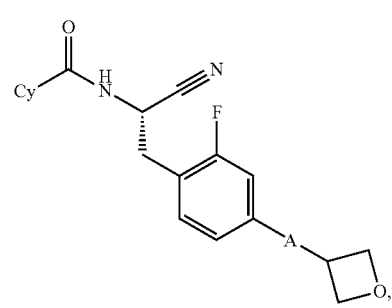

and their use as inhibitors of Cathepsin C, pharmaceutical compositions containing the same, and methods of using the same as agents for treatment and/or prevention of diseases connected with dipeptidyl peptidase I activity, e.g. respiratory diseases.

8 Claims, No Drawings

(56) References Cited

OTHER PUBLICATIONS

Farberman, M.M. et al., "Airway proteins involved in bacterial clearance susceptible to cathepsin G proteolysis." European Respiratory Journal, 2010, vol. 35, No. 2, pp. 410-417.

Guay, D. et al., "Design and synthesis of dipeptidyl nitriles as potent, selective, and reversible inhibitors of cathespin C." Bioorganic & Medicinal Chemistry Letters, 2009, vol. 19, No. 18, pp. 5392-5396.

Guyot, N. et al., "Deficiency in All Three Neutrophil Serine Proteases Protects Mice Against Cigarette Smoke-Induced Emphysema." American Journal of Respiratory and Critical Care Medicine, 2010, vol. 181, p. A5128.

Henriksen, P.A. et al., "Human neutrophil elastase: Mediator and therapeutic target in atherosclerosis." The International Journal of Biochemistry & Cell Biology, 2008, vol. 40, pp. 1095-1100.

Herias, M. et al., "Abstract 5871: Leukocyte Cathepsin C Deficiency Attenuates Atherosclerosis in LDL Receptor Deficient Mice." Circulation, 2009, vol. 120, p. 1166.

Hu, Y. et al., "Dipeptidyl Peptidase I Regulates the Development of Collagen-Induced Arthritis." Arthritis & Rheumatism, 2005, vol. 52, No. 8, pp. 2553-2558.

International Search Report and Written Opinion for PCT/EP2015/067271 mailed Sep. 22, 2015.

Joosten, L.A. et al., "Inflammatory Arthritis in Caspase 1 Gene-Deficient Mice." Arthritis & Rheumatism, 2009, vol. 60, No. 12, pp. 3651-3662.

Koga, H. et al., "Inhibition of neutrophil elastase attenuates airway hyperresponsiveness and inflammation in a mouse model of secondary allergen challenge: neutrophil elastase inhibition attenuates allergic airway responses." Respiratory Research, 2013, vol. 14, No. 8, pp. 1-13.

Kotlowski, R. et al., "Population-Based Case-Control Study of Alpha 1-Antitrypsin and SLC11A1 in Crohn's Disease and Ulcerative Colitis." Inflammatory Bowel Disease, 2008, vol. 14, No. 8, pp. 1112-1117.

Laprise, C. et al., "Functional classes of bronchial mucosa genes that are differentially expressed in asthma." BMC Genomics, 2004, vol. 5, No. 21, pp. 1-10.

Liu, H. et al., "Neutrophil elastase and elastase-rich cystic fibrosis sputum degranulate human eosinophils in vitro." American Physiological Scoiety, 1999, vol. 276, pp. L28-L34.

Milner, J.M. et al., "Emerging Roles of Serine Proteinases in Tissue Turnover in Arthritis." Arthritis & Rheumatism, 2008, vol. 58, No. 12, pp. 3644-3656.

Morohoshi, Y. et al., "Inhibition of neutrophil elastase prevents the development of murine dextran sulfate sodium-induced colitis." Journal of Gastroenterology, 2006, vol. 41, pp. 318-324.

Motta, Jean-Paul et al., "Modifying the Protease, Antiprotease Pattern by Elafin Overexpression Protects Mice From Colitis." Gastroenterology, 2011, vol. 140, pp. 1272-1282.

Schmid, M. et al., "Attenuated induction of epithelial and leukocyte serine antiproteases elafin and secretory leukocyte protease inhibitor in Crohn's disease." Journal of Leukocyte Biology, 2007, vol. 81, pp. 907-915.

Sedor, J. et al., "Cathepsin-G Interferes with Clearance of Pseudomonas aeruginosa from Mouse Lungs." Pediatric Research, 2007, vol. 61, No. 1, pp. 26-31.

Shapiro, S.D. et al., "Neutrophil Elastase Contributes to Cigarette Smoke-Induced Emphysema in Mice." American Journal of Pathology, 2003, vol. 163, No. 6, pp. 2329-2335.

Wright, J.L. et al., "Synthetic Serine Elastase Inhibitor Reduces Cigarette Smoke-Induced Emphysema in Guinea Pigs." Ameican Journal of Respiratory and Critical Care Medicine, 2002, vol. 166, pp. 954-960.

Yuyama, N. et al., "Analysis of Novel Disease-Related Genes in Bronchial Asthma." Cytokine, 2002, vol. 19, No. 6, pp. 287-296.

SUBSTITUTED OXETANES AND THEIR USE AS INHIBITORS OF CATHEPSIN C

RELATED APPLICATIONS

This application claims priority to foreign application No. EP 14179458.6 filed Aug. 1, 2014, the entire content of which is incorporated herein by reference in its entirety as though fully set forth herein.

FIELD OF INVENTION

This invention relates to a compound of formula I

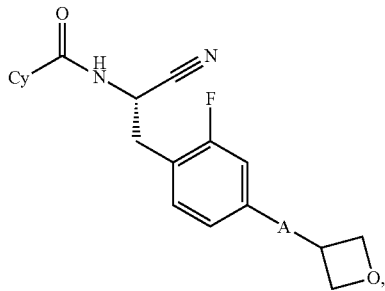

and their use as inhibitors of Cathepsin C, pharmaceutical compositions containing the same, and methods of using the same as agents for treatment and/or prevention of diseases connected with dipeptidyl peptidase I activity, e.g. respiratory diseases

BACKGROUND INFORMATION

WO2004110988 discloses peptidyl nitrile inhibitors as dipeptidyl-peptidase I (DPPI) inhibitors for the treatment of a series of diseases.

WO2009074829 and WO2010142985 also disclose peptidyl nitrile inhibitors as dipeptidyl-peptidase I (DPPI) inhibitors for the treatment asthma, COPD or allergic rhinitis.

BRIEF SUMMARY OF THE INVENTION

Dipeptidyl-aminopeptidase I (DPPI or Cathepsin C; EC3.4.141), is a lysosomal cysteine protease capable of removing dipeptides from the amino terminus of protein substrates. DPPI was first discovered by Gutman and Fruton in 1948 (J. Biol. Chem 174: 851-858, 1948). The cDNA of the human enzyme has been described in 1995 (Paris et al.; FEBS Lett 369: 326-330, 1995). The DPPI protein is processed into a mature proteolytically active enzyme consisting of a heavy chain, a light chain, and a propeptide that remains associated with the active enzyme (Wolters et al.; J. Biol. Chem. 273: 15514-15520, 1998). Whereas the other cysteine Cathepsins (e.g. B, H, K, L and S) are monomers, DPPI is a 200-kD tetramer with 4 identical subunits, each composed of the 3 different polypeptide chains. DPPI is constitutively expressed in many tissues with highest levels in lung, kidney, liver and spleen (Kominami et al.; Biol. Chem. Hoppe Seyler 373: 367-373, 1992). Consistent with its role in the activation of serine proteases from hematopoetic cells, DPPI is also relatively highly expressed in neutrophils, cytotoxic lymphocytes, natural killer cells, alveolar macrophages and mast cells. Recent data from DPPI deficient mice suggest that, besides being an important enzyme in lysosomal protein degradation, DPPI also functions as the key enzyme in the activation of granule serine proteases in cytotoxic T lymphocytes and natural killer cells (granzymes A and B; Pham et al.; Proc. Nat. Acad. Sci 96: 8627-8632, 1999), mast cells (chymase and tryptase; Wolter et al.; J Biol. Chem. 276: 18551-18556, 2001), and neutrophils (Cathepsin G, elastase and proteinase 3; Adkison et al.; J Clin. Invest. 109: 363.371, 2002). Once activated, these proteases are capable of degrading various extracellular matrix components, which can lead to tissue damage and chronic inflammation.

Thus, inhibitors of Cathepsin C could potentially be useful therapeutics for the treatment of neutrophil-dominated inflammatory diseases such as chronic obstructive pulmonary disease (COPD), pulmonary emphysema, asthma, multiple sclerosis, and cystic fibrosis (Guay et al.; Curr. Topics Med. Chem. 10: 708-716, 2010; Laine and Busch-Petersen; Expert Opin. Ther. Patents 20: 497-506, 2010). Rheumatoid arthritis is also another chronic inflammatory disease where DPPI appears to play a role. Neutrophils are recruited to the site of joint inflammation and release Cathepsin G, elastase and proteinase 3, proteases which are believed to be responsible for cartilage destruction associated with rheumatoid arthritis. Indeed, DPPI deficient mice were protected against acute arthritis induced by passive transfer of monoclonal antibodies against type II collagen (Adkison et al.; J Clin. Invest. 109: 363.371, 2002).

In light of the role DPPI plays in activating certain pro-inflammatory serine proteases, the problem of the present invention is to prepare compounds that inhibit its activity, which thereby inhibit downstream serine protease activity. It has been surprisingly found that the bicyclic compounds of the present invention possess potent Cathepsin C activity, high selectivity against other Cathepsins, e.g. Cathepsin K, and in general desirable pharmacokinetic properties.

DETAILED DESCRIPTION OF THE INVENTION

It has surprisingly been found that the problem mentioned above is solved by compounds of formula (I) of the present invention.

The present invention therefore relates to a compound of formula I

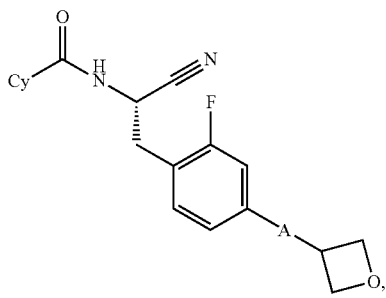

wherein
Cy denotes a group of formula Cy¹ or Cy²,

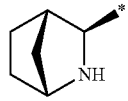

(Cy¹)

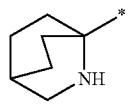

(Cy²)

A denotes a 5 to 10 membered monocyclic, bicyclic or spirocyclic heterocycle containing 1 or 2 N-atoms, preferably a 5 to 8 membered monocyclic, bicyclic or spirocyclic heterocycle, or a salt, solvates or hydrates thereof.

PREFERRED EMBODIMENTS

Preferred are the above compounds of formula I, wherein A denotes a group of formula (a) or (b),

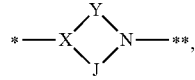

(a)

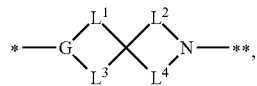

(b)

X is selected from among N, —CH— and =C—
Y is selected from among —(CH$_2$)$_m$— or =CH—(CH$_2$)$_n$—
J denotes —(CH$_2$)$_o$—
Y and J are optionally linked by a bond or —(CH$_2$)$_p$—
m, n, o independently from each other denote 1, 2, 3 or 4,
p denotes 1 or 2,
G denotes N or —CH—
L¹, L², L³, L⁴ independently from each other denote —CH$_2$— or —CH$_2$—CH$_2$—
or a salt thereof.

Preferred are the above compounds of formula I, wherein A denotes a group of formula (a.I)

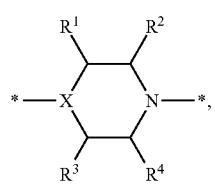

(a.I)

X denotes N or —CH—
R¹, R², R³, R⁴ independently from each other denote H or optionally one pair selected from among R¹ and R³, R¹ and R⁴, R² and R³ and R² and R⁴ together denotes (—CH$_2$—) or —CH$_2$—CH$_2$—.
or a salt thereof.

Preferred are the above compounds of formula I, wherein A denotes a group of formula (a.II)

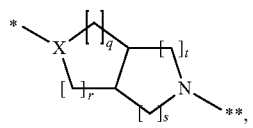

(a.II)

X denotes N or —CH—
q, s independently from each other denote 0, 1 or 2
t, r independently from each other denote 1 or 2,
or a salt thereof.

Preferred are the above compounds of formula I, wherein A denotes a group of formula (b).

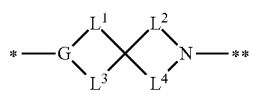

(b)

selected from among formulas (b.1) to (b.12).

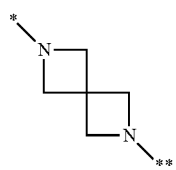

(b.1)

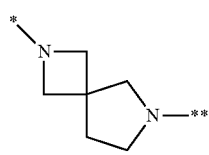

(b.2)

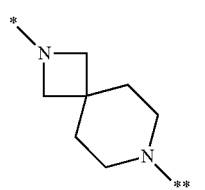

(b.3)

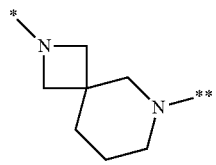

(b.4)

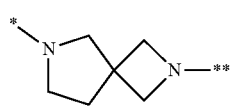

(b.5)

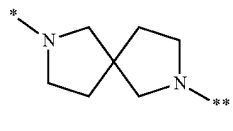

(b.6)

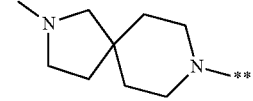

(b.7)

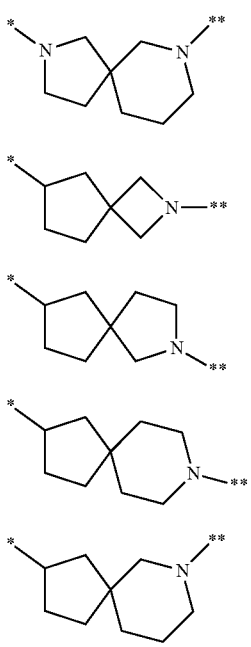
(b.8)
(b.9)
(b.10)
(b.11)
(b.12)
Preferred are the above compounds of formula I, wherein A denotes a group of formula (b.I),
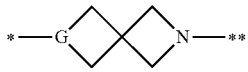
(b.I)
G denotes N or —CH—
or a salt thereof.
Preferred are the above compounds of formula I, wherein A denotes a group of formula (a).
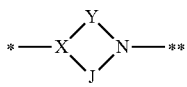
(a)
selected from among formulas (a.1) to (a.60).
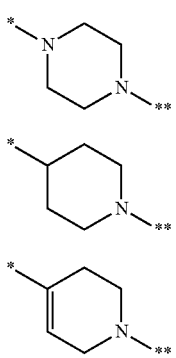
(a.1)
(a.2)
(a.3)
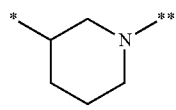
(a.4)
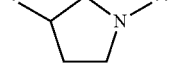
(a.5)
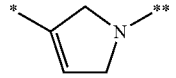
(a.6)
(a.7)
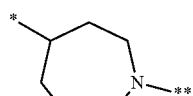
(a.8)
(a.9)
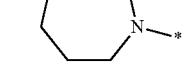
(a.10)
(a.11)
(a.12)
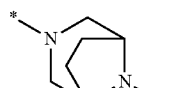
(a.13)
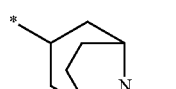
(a.14)
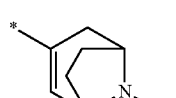
(a.15)
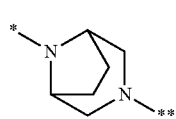
(a.16)

-continued
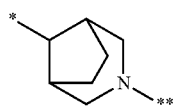 (a.17)
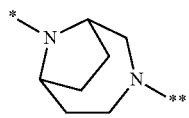 (a.18)
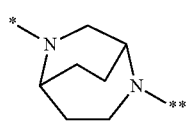 (a.19)
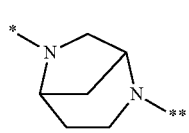 (a.20)
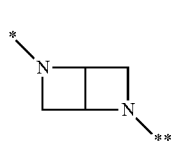 (a.21)
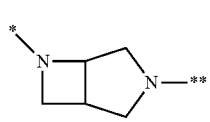 (a.22)
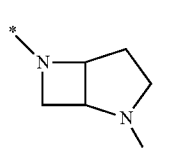 (a.23)
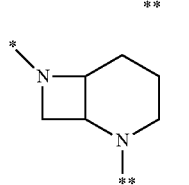 (a.24)
(a.25)
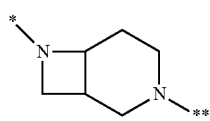
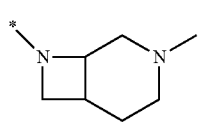 (a.26)
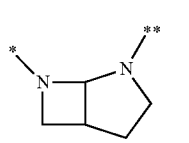 (a.27)
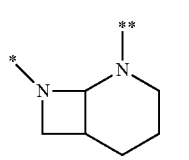 (a.28)
-continued
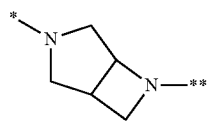 (a.29)
(a.30)
(a.31)
(a.32)
(a.33)
(a.34)
(a.35)
(a.36)
(a.37)
(a.38)
(a.39)

(a.40) 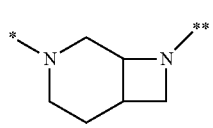
(a.41) 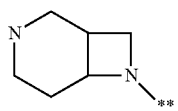
(a.42) 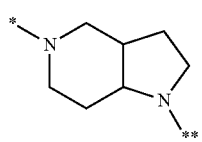
(a.43) 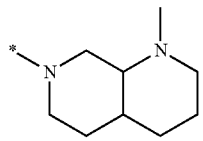
(a.44) 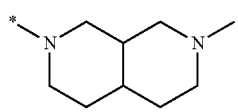
(a.45) 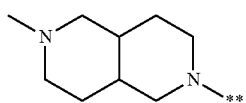
(a.46) 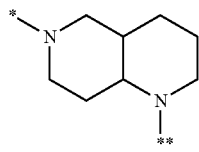
(a.47) 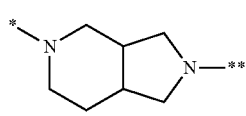
(a.48) 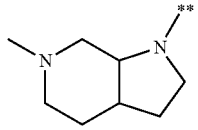
(a.49) 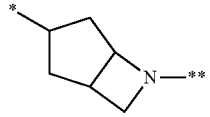
(a.50) 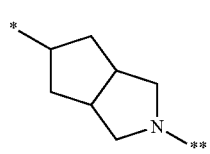
(a.51) 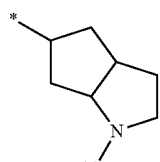
(a.52) 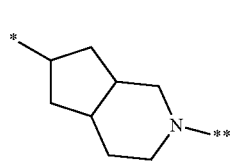
(a.53) 
(a.54) 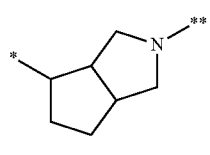
(a.55)
(a.56) 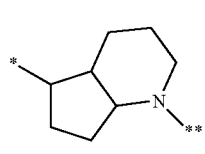
(a.57) 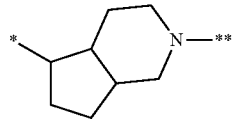
(a.58) 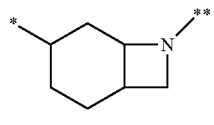
(a.59) 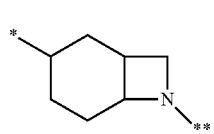
(a.60) 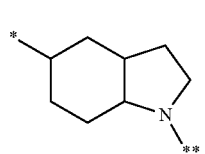
Preferred are the above compounds of formula I, wherein A denotes a group of formula (a).

(a)
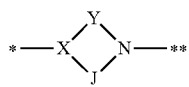
selected from among formulas (a.61) to (a.91).
(a.61)
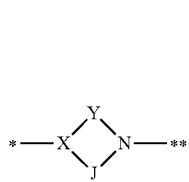
(a.62)
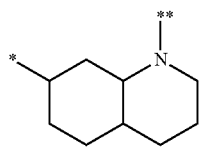
(a.63)
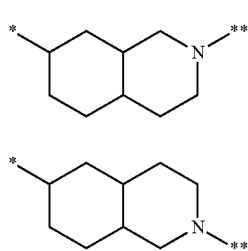
(a.64)
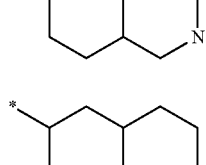
(a.65)
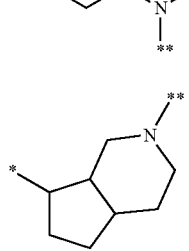
(a.66)
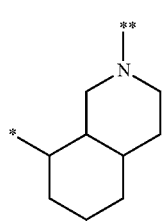
(a.67)
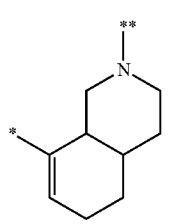
(a.68)
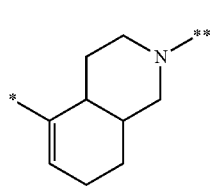
(a.69)
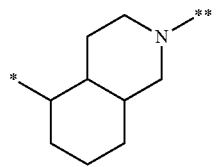
(a.70)
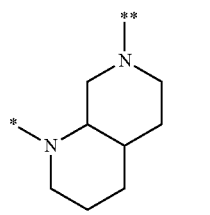
(a.71)
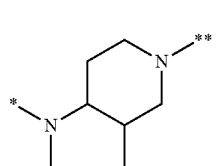
(a.72)
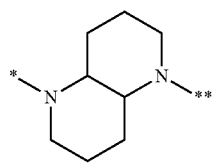
(a.73)
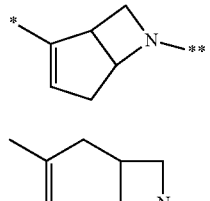
(a.74)
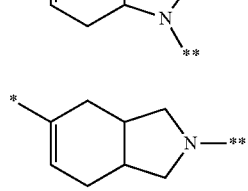
(a.75)
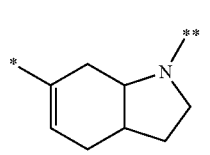
(a.76)
(a.77)
(a.78)

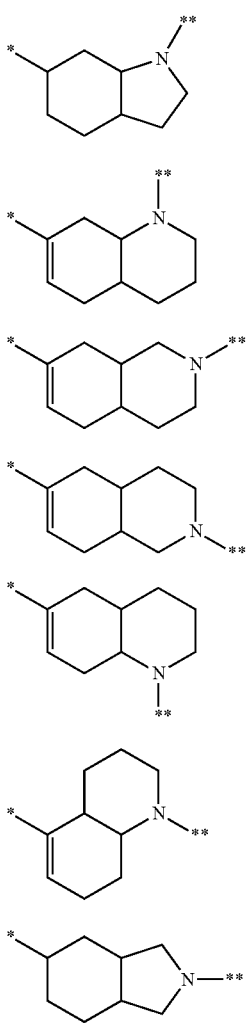
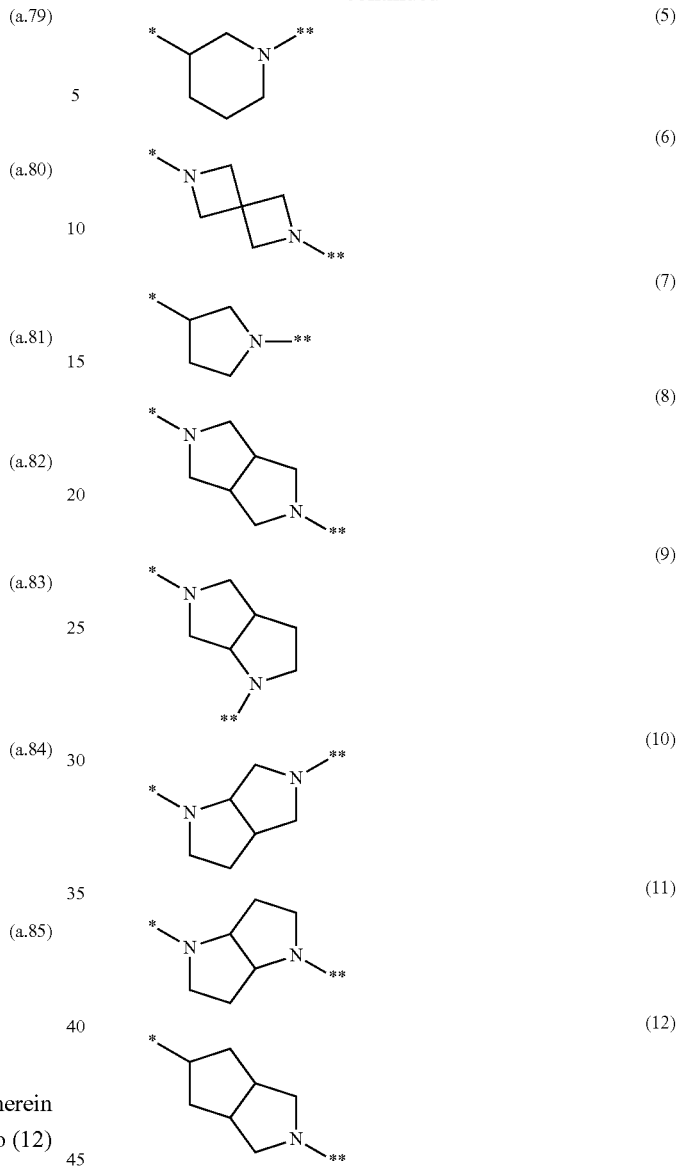
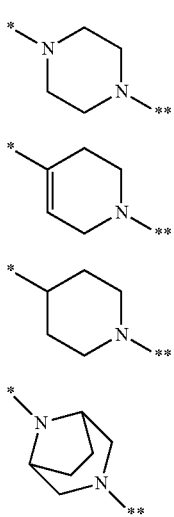

Preferred are the above compounds of formula I, wherein A denotes a group selected from among formulas (1) to (12)

or a salt thereof.
Preferred are the above compounds of formula I, wherein A denotes a group of formula (6).
Preferred are the above compounds of formula I, wherein Cy denotes a group of formula $Cy^1$.
Preferred are the above compounds of formula I, wherein Cy denotes a group of formula $Cy^2$.
Preferred are the above compounds of formula I, wherein A denotes a group of formula (a).
Preferred are the above compounds of formula I, wherein A denotes a group of formula (b).
Preferred are the above compounds of formula I, wherein X denotes N or CH.
Particularly preferred are the above compounds of formula I, wherein X denotes N.
Preferred are the above compounds of formula I, wherein Y denotes —$(CH_2)_2$—.
Preferred are the above compounds of formula I, wherein J denotes —$(CH_2)_2$— or —$(CH_2)_3$—.

Preferred are the above compounds of formula I, wherein Y and J are linked by a bond or —(CH2)$_p$-, more preferably Y and J are linked by a bond or —(CH$_2$)$_2$—.

Preferred are the above compounds of formula I, wherein G denotes N.

Preferred are the above compounds of formula I, wherein m denotes 2 or 3.

Preferred are the above compounds of formula I, wherein n denotes 1.

Preferred are the above compounds of formula I, wherein o denotes 2 or 3.

Preferred are the above compounds of formula I, wherein p denotes 2.

Preferred are the above compounds of formula I, wherein q, r, s, t denote 1.

Preferred are the above compounds of formula I, wherein $L^1$, $L^2$, $L^3$, $L^4$ denote —CH$_2$—.

Preferred are the above compounds of formula I, wherein two substituents of $R^1$, $R^2$, $R^3$ and $R^4$ independently from each other denote H and one pair selected from among $R^1$ and $R^3$, $R^1$ and $R^4$, $R^2$ and $R^3$ and $R^2$ and $R^4$ together denotes —CH$_2$— or —CH$_2$—CH$_2$—, preferably —CH$_2$—CH$_2$—.

Particularly preferred are the compounds of formula I, wherein Cy denotes Cy$^1$ and A denotes a group selected from among formulas (1) to (12).

Particularly preferred are the compounds of formula I, wherein the compounds are selected from the group consisting of examples 1, 2, 3, 5, 7 and 16.

Any and each other of the definitions of $R^1$ to $R^4$, Cy, Cy1, Cy2, A, (a), (b), X, Y, G, J, m, n, o, p, q, r, s, t, $L^1$, $L^2$, $L^3$ and $L^4$ may be combined with each other.

A further embodiment of the current invention is a compound of formula I or a pharmaceutically acceptable salt thereof for use as a medicament.

A further embodiment of the current invention is a compound of formula 1 for use as a medicament for the treatment of asthma and allergic diseases, gastrointestinal inflammatory diseases, glomerulonephritis, eosinophilic diseases, chronic obstructive pulmonary disease, infection by pathogenic microbes, rheumatoid arthritis, neutrophilic diseases, cystic fibrosis (CF), non-CF bronchiectasis, idiopathic pulmonary fibrosis, bronchiectasis, ANCA-associated vasculitis, lung cancer, emphysema, chronic bronchitis, acute lung injury (ALI), acute respiratory distress syndrome (ARDS), pulmonary hypertension, pulmonary arterial hypertension (PAH) and Alpha-1-antitrypsin deficiency (AATD), obesity and related inflammation (e.g. related inflammation e.g. chronic adipose tissue inflammation, adipose inflammation and high-fat diet induced inflammation), insulin resistance, diabetes, fatty liver, liver steatosis and inflammatory or neuropathic pain, traumatic brain injury and abdominal aortic aneurism.

Preferred is a compound of formula I or a pharmaceutically acceptable salt thereof for use as a medicament for the treatment of asthma and allergic diseases, gastrointestinal inflammatory diseases, eosinophilic diseases, chronic obstructive pulmonary disease, infection by pathogenic microbes, rheumatoid arthritis and atherosclerosis.

A further embodiment of the current invention is a pharmaceutical composition, characterised in that it contains one or more compounds of formula or a pharmaceutically active salt thereof.

A further embodiment of the current invention is a method of treatment or prevention of diseases in which DPPI activity inhibitors have a therapeutic benefit, which method comprises administration of a therapeutically or preventively effective amount of a compounds of formula 1 to a patient in need thereof.

A further embodiment of the current invention is a pharmaceutical composition comprising additionally to a compound of formula I, a pharmaceutically active compound selected from the group consisting of betamimetics, anticholinergics, corticosteroids, PDE4-inhibitors, LTD4-antagonists, EGFR-inhibitors, CRTH2 inhibitors, 5-LO-inhibitors, Histamine receptor antagonists, CCR9 antagonists and SYK-inhibitors, NE-inhibitors, MMP9 inhibitors and MMP12 inhibitors, but also combinations of two or three active substances.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

Alternatively "*" indicates within a chemical entity the binding site, i.e. the point of attachment "*" indicates within a chemical entity the binding site, i.e. the point of attachment, to the oxetane group of formula I.

In case a compound of the present invention is depicted in form of a chemical name and as a formula in case of any discrepancy the formula shall prevail. An asterisk is may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (-)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (-)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term "$C_{1-n}$-alkyl", wherein n is an integer selected from 2, 3, 4, 5 or 6, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{5-10}$-heterocycle" means a saturated or unsaturated mono- or polycyclic-ring systems including aromatic ring system containing one or more heteroatoms independently selected from N, O or $S(O)_r$, wherein r=0, 1 or 2, consisting of 5 to 10 ring atoms wherein none of the heteroatoms is part of the aromatic ring. The term "heterocycle" is intended to include all the possible isomeric forms. Thus, the term "heterocycle" includes the following exemplary structures which are not depicted as radicals as each form may be attached through a covalent (single or double) bond to any atom so long as appropriate valences are maintained:

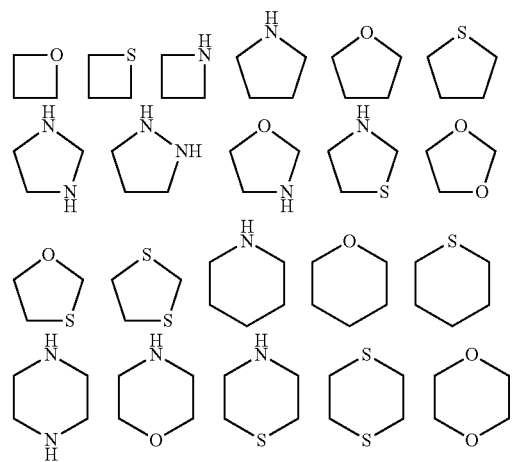

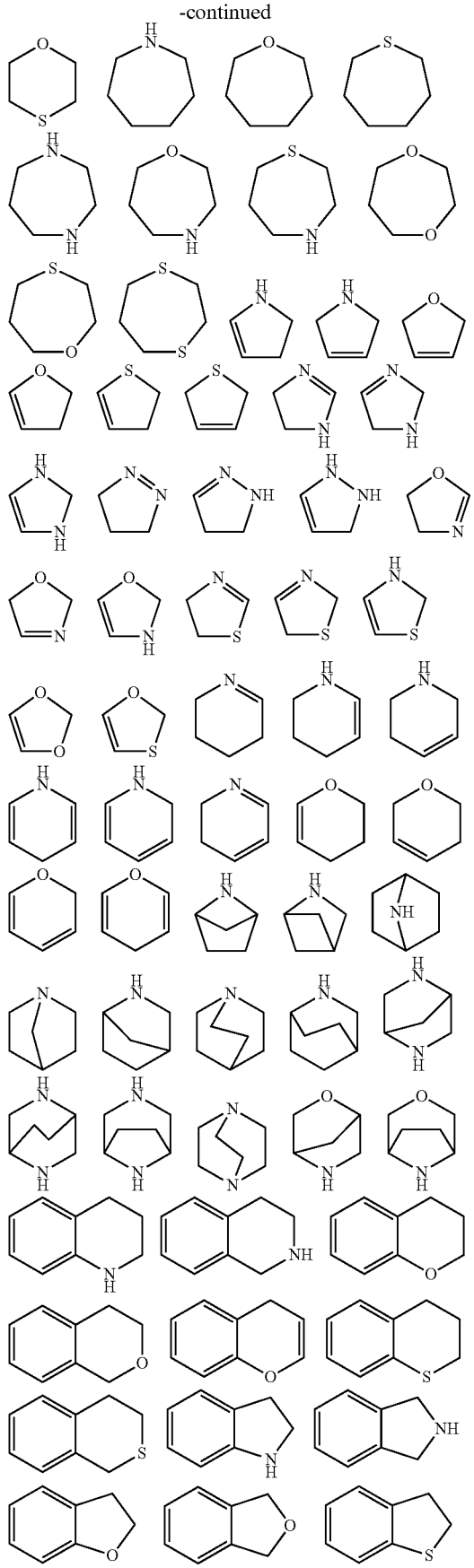
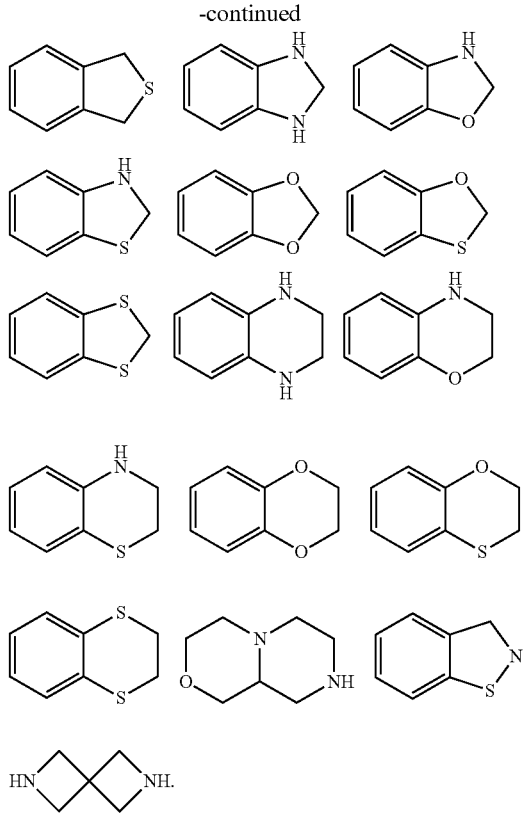

Preparation

General Synthetic Methods

The invention also provides processes for making a compound of Formula I. In all methods, unless specified otherwise A shall have the meaning of A in Formula I of the invention described herein above.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

A compound of Formula I may be made by the method outlined in Scheme 1, 2 or 3:

Scheme 1

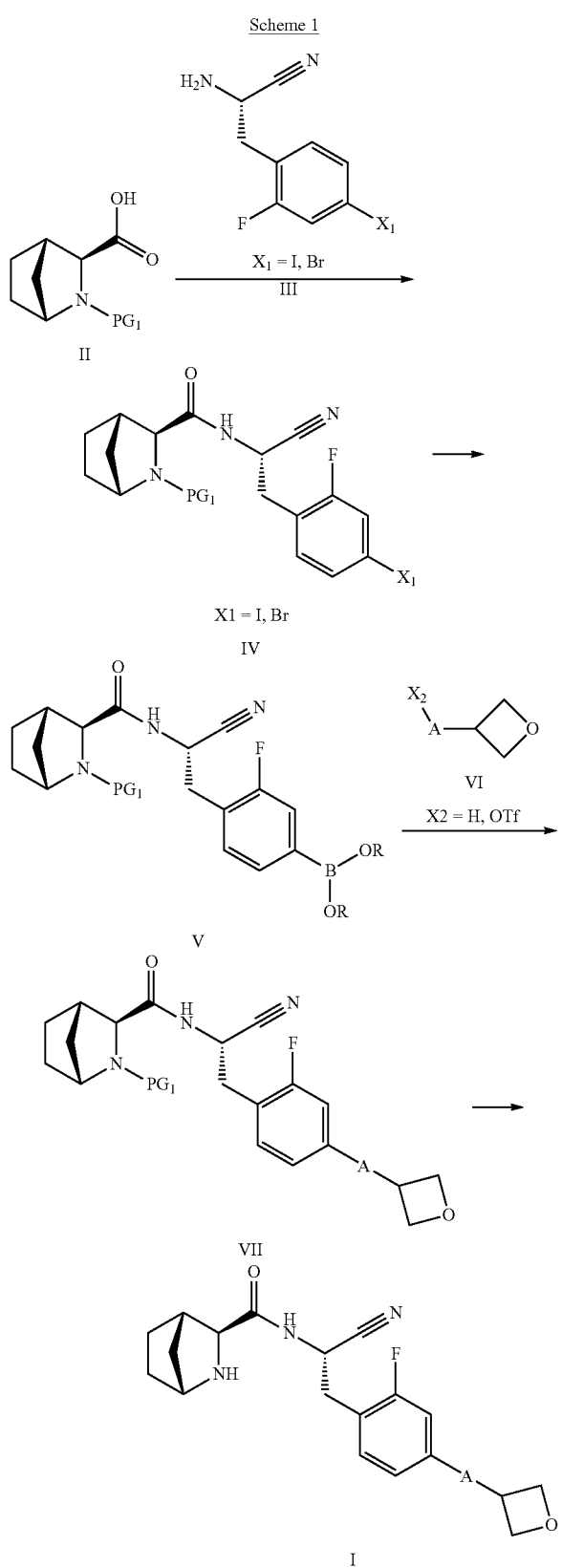

example in the presence of a base such as N, N-diisopropylethylamine (DIPEA) and an activating agent such as HATU or TBTU, with an amine of Formula III in a suitable solvent, provides a compound of Formula IV. Standard peptide coupling reactions known in the art (see for example M. Bodanszky, 1984, The Practice of Peptide Synthesis, Springer-Verlag) may be employed in these syntheses.

Compounds of formula IV (X1=I, Br) can be converted into the corresponding boronic acid derivatives V, wherein R can be H or $C_{1-3}$-alkyl independently and the residues R can form a ring. For example, IV can be reacted with bis(neopentyl glycolato)diboron in the presence of a suitable catalyst such as [1,1'-bis(diphenylphosphino)ferrocene]dichloropalladium(II), and a suitable base such as potassium acetate or sodium, potassium or cesium carbonate or phosphate, in a suitable solvent such as dioxan, dimethylformamide (DMF), or dichloromethane (DCM) to yield the boronic esters V.

These can be reacted in a (transition) metal catalyzed reaction of a compound of Formula VI. Wherein the connecting point is a nitrogen (X2 is H) may be reacted in the presence of a suitable catalyst such as Cu(II)acetate and a suitable base such as TEA provides a compound of Formula VII.

Wherein the connecting point is a carbon, a ketone group of the precursor of VI can be converted to a trifluoromethanesulfonyl group (X2=OTf) at any level. Especially, a precurser compound of VI with X2=O is transformed to the appropriate triflate of the corresponding enol (X2=OTf) by reaction with e.g. N,N-bis-(trifluoromethanesulfonyl) aniline in the presence of an organic base e.g. lithium bis(trimethylsilyl)amide in an appropriate anhydrous solvent, e.g. THF. Coupling of these triflates provide a compound of Formula VII. For example, reaction of these triflats with a boronic acid or the corresponding boronic acid ester V, in a suitable solvent such as dioxane, in the presence of a suitable catalyst such as 1,1'-Bis(diphenylphosphino)ferrocene-dichloropalladium(II) and a suitable base such as $Na_2CO_3$ provides a compound of Formula VII. The protection and deprotection of functional groups is described in 'Protective Groups in Organic Synthesis', T. W. Greene and P. G. M. Wuts, Wiley-Interscience. For example, for the deprotection of tert-butoxycarbonyl, an acid such as p-toluenesulfonic acid monohydrate may be used in a suitable solvent such as acetonitrile.

Scheme 2

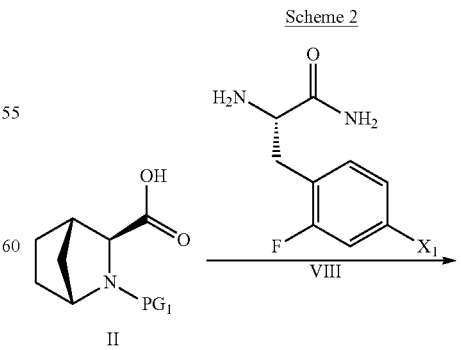

Reacting an acid of Formula II, wherein PG1 represents a protecting group (e.g. tert-butoxycarbonyl) using standard literature procedures for the formation of an amide, for

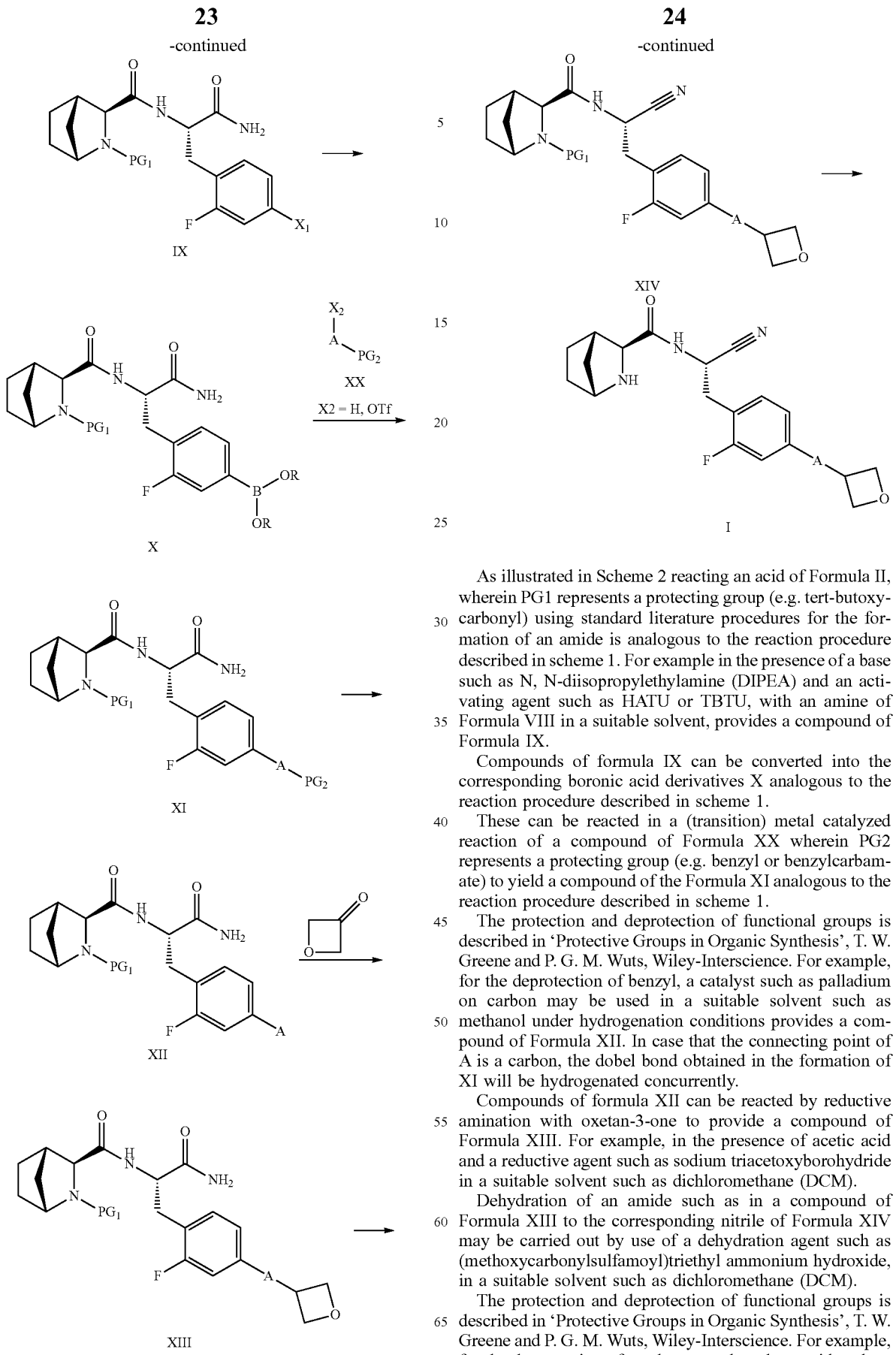

As illustrated in Scheme 2 reacting an acid of Formula II, wherein PG1 represents a protecting group (e.g. tert-butoxycarbonyl) using standard literature procedures for the formation of an amide is analogous to the reaction procedure described in scheme 1. For example in the presence of a base such as N, N-diisopropylethylamine (DIPEA) and an activating agent such as HATU or TBTU, with an amine of Formula VIII in a suitable solvent, provides a compound of Formula IX.

Compounds of formula IX can be converted into the corresponding boronic acid derivatives X analogous to the reaction procedure described in scheme 1.

These can be reacted in a (transition) metal catalyzed reaction of a compound of Formula XX wherein PG2 represents a protecting group (e.g. benzyl or benzylcarbamate) to yield a compound of the Formula XI analogous to the reaction procedure described in scheme 1.

The protection and deprotection of functional groups is described in 'Protective Groups in Organic Synthesis', T. W. Greene and P. G. M. Wuts, Wiley-Interscience. For example, for the deprotection of benzyl, a catalyst such as palladium on carbon may be used in a suitable solvent such as methanol under hydrogenation conditions provides a compound of Formula XII. In case that the connecting point of A is a carbon, the dobel bond obtained in the formation of XI will be hydrogenated concurrently.

Compounds of formula XII can be reacted by reductive amination with oxetan-3-one to provide a compound of Formula XIII. For example, in the presence of acetic acid and a reductive agent such as sodium triacetoxyborohydride in a suitable solvent such as dichloromethane (DCM).

Dehydration of an amide such as in a compound of Formula XIII to the corresponding nitrile of Formula XIV may be carried out by use of a dehydration agent such as (methoxycarbonylsulfamoyl)triethyl ammonium hydroxide, in a suitable solvent such as dichloromethane (DCM).

The protection and deprotection of functional groups is described in 'Protective Groups in Organic Synthesis', T. W. Greene and P. G. M. Wuts, Wiley-Interscience. For example, for the deprotection of tert-butoxycarbonyl, an acid such as p-toluenesulfonic acid monohydrate may be used in a suitable solvent such as acetonitrile.

Scheme 3

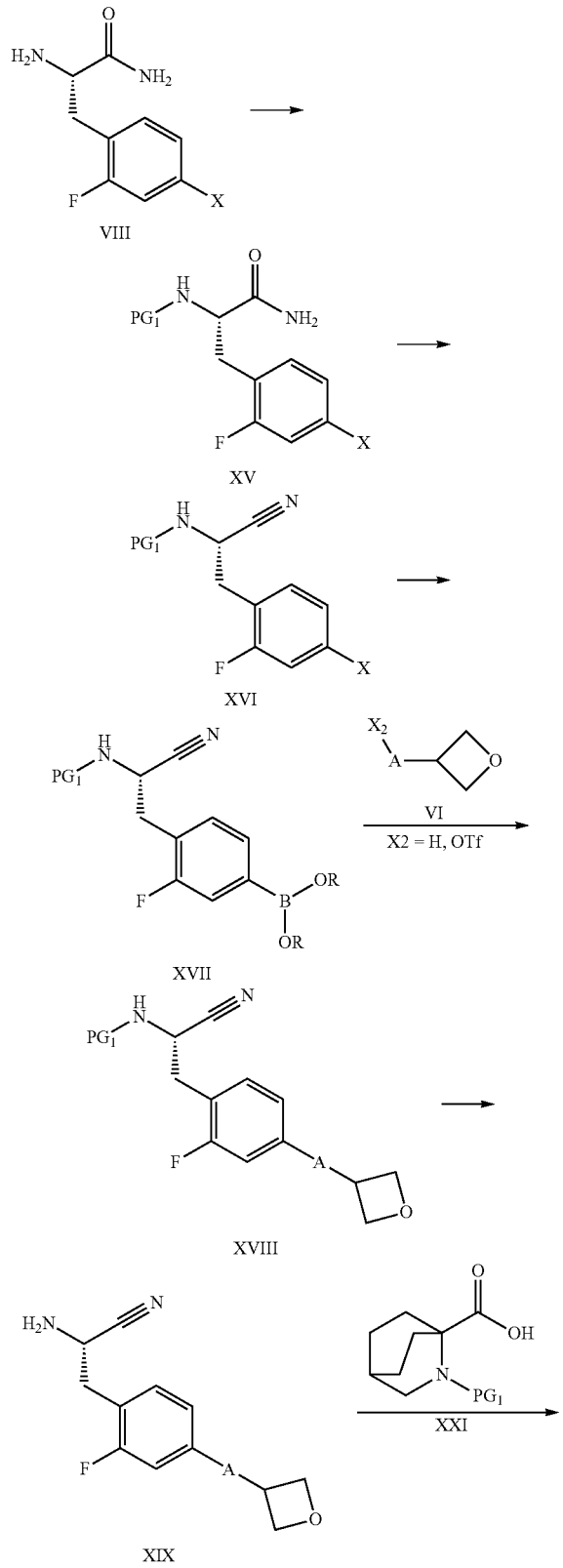

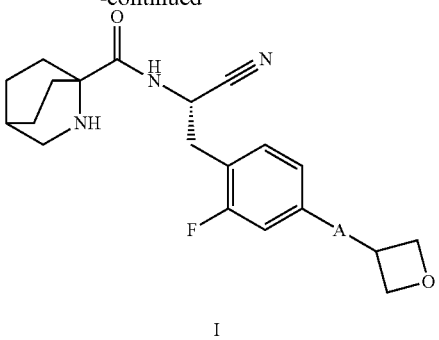

X = Br, I

As illustrated in Scheme 3 the protection and deprotection of functional groups is described in 'Protective Groups in Organic Synthesis', T. W. Greene and P. G. M. Wuts, Wiley-Interscience. For example, for the protection of tert-butoxycarbonyl, an amin such as in a compound of Formula VIII di-tert-butyl dicarbonate may be used in a suitable solvent such as dichloromethane and a suitable base such as DIPEA to provide a compound of Formula XV.

Dehydration of an amide such as a compound of Formula XV to the corresponding nitrile of Formula XVI may be carried out by use of a dehydration agent such as (methoxycarbonylsulfamoyl)triethyl ammonium hydroxide, in a suitable solvent such as dichloromethane (DCM).

Compounds of formula XVI can be converted into the corresponding boronic acid derivatives XVII, wherein R can be H or $C_{1-3}$-alkyl independently and the residues R can form a ring. For example, XVI can be reacted with bis(neopentyl glycolato)diboron in the presence of a suitable catalyst such as [1,1'-bis(diphenylphosphino)ferrocene]dichloropalladium(II), and a suitable base such as potassium acetate or sodium, potassium or cesium carbonate or phosphate, in a suitable solvent such as dioxan, dimethylformamide (DMF), or dichloromethane (DCM) to yield the boronic esters XVII.

These can be reacted in a (transition) metal catalyzed reaction of a compound of Formula VI analogous to the reaction procedure described in scheme 1 to yield a compound of Formula XVIII.

The protection and deprotection of functional groups is described in 'Protective Groups in Organic Synthesis', T. W. Greene and P. G. M. Wuts, Wiley-Interscience. For example, for the deprotection of tert-butoxycarbonyl, an acid such as trifluoro acetic acid may be used in a suitable solvent such as acetonitrile to provide a compound of Formula XIX.

Reacting an acid of Formula XXI, wherein PG1 represents a protecting group (e.g. tert-butoxycarbonyl) using standard literature procedures for the formation of an amide, for example in the presence of a base such as N-methylmorpholine and an activating agent such as 1-propanephosphonic acid cyclic anhydride (PPA), with an amine of Formula XIX in a suitable solvent, provides a compound of Formula I. Standard peptide coupling reactions known in the art (see for example M. Bodanszky, 1984, The Practice of Peptide Synthesis, Springer-Verlag) may be employed in these syntheses.

Further modifications of compounds of Formula I by methods known in the art and illustrated in the Examples below, may be used to prepare additional compounds of the invention.

Synthetic Examples

The following are representative compounds of the invention which can be made by the general synthetic schemes, the examples, and known methods in the art. Starting materials and intermediates were either commercially available and purchased from catalogues of ABCR, ACROS, ACTIVATE, ALDRICH, APAC, APOLLO SCIENTIFIC, AQUILA PHARMA, ARK PHARMA, CHEM-IMPEX, ENAMINE, FLUKA, GOLDENBRIDGE, MERCK, NETCHEM, WUXI or were synthesized according to literature or as described below in "Synthesis of starting materials/educts"

Liquid chromatography-mass spectroscopy (LCMS) retention time and observed m/z data for the compounds below are obtained by one of the following methods:

| LC-MS Method 003_CA04 | | | | |
|---|---|---|---|---|
| Device-Description | Agilent 1100 with DAD and MSD | | | |
| Column | Waters XBridge C18 | | | |
| Column Dimension | 3.0 × 30 mm | | | |
| Particle Size | 2.5 µm | | | |
| Gradient/ Solvent Time [min] | % Sol [$H_2O$ 0.1% $NH_4OH$] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

| LC-MS Method 004_CA05 | | | | |
|---|---|---|---|---|
| Device-Description | Waters Acquity with DAD and MSD, CTC Autosampler | | | |
| Column | Waters XBridge C18 | | | |
| Column Dimension | 3.0 × 30 mm | | | |
| Particle Size | 2.5 µm | | | |
| Gradient/ Solvent Time [min] | % Sol [$H_2O$ 0.1% $NH_4OH$] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

| LC-MS Method V011_S01 | | | | |
|---|---|---|---|---|
| Device-Description | Waters Alliance with DAD and MSD | | | |
| Column | Waters XBridge C18 | | | |
| Column Dimension | 4.6 × 30 mm | | | |
| Particle Size | 3.5 µm | | | |
| Solvent Gradient time [min] | % Sol [$H_2O$, 0.1% $NH_3$] | % Sol [Acetonitril] | Flow [ml/min] | Temp [° C.] |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| LC-MS Method V012_S01 | | | | |
|---|---|---|---|---|
| Device-Description | Waters Alliance with DAD and MSD | | | |
| Column | Waters XBridge C18 | | | |
| Column Dimension | 4.6 × 30 mm | | | |
| Particle Size | 3.5 µm | | | |
| Solvent Gradient time [min] | % Sol [$H_2O$, 0.1% TFA] | % Sol [Acetonitril] | Flow [ml/min] | Temp [° C.] |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| LC-MS Method X011_S03 | | | | |
|---|---|---|---|---|
| Device-Description | Waters Acquity with DAD and MSD | | | |
| Column | Waters Xbridge BEH C18 | | | |
| Column Dimension | 2.1 × 30 mm | | | |
| Particle Size | 1.7 µm | | | |
| Solvent Gradient time [min] | % Sol [H2O, 0.1% $NH_3$] | % Sol [Acetonitril] | Flow [ml/min] | Temp [° C.] |
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

| LC-MS Method X018_S01 | | | | |
|---|---|---|---|---|
| Device-Description | Waters Acquity with DAD and MSD | | | |
| Device-Description | Waters Acquity with DAD and MSD | | | |
| Column | Waters Sunfire C18 | | | |
| Column Dimension | 2.1 × 30 mm | | | |
| Particle Size | 2.5 µm | | | |
| Gradient/ Solvent Time [min] | % Sol [$H_2O$, 0.1% TFA] | % Sol [Acetonitril] | Flow [ml/min] | Temp [° C.] |
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

| LC-MS Method X018_S02 | | | | |
|---|---|---|---|---|
| Device-Description | Waters Acquity with DAD and MSD | | | |
| Column | Waters Sunfire C18 | | | |
| Column Dimension | 2.1 × 30 mm | | | |
| Particle Size | 2.5 µm | | | |
| Gradient/ Solvent Time [min] | % Sol [$H_2O$, 0.1% TFA] | % Sol [Acetonitril] | Flow [ml/min] | Temp [° C.] |
| 0.0 | 99 | 1 | 1.3 | 60 |
| 0.02 | 99 | 1 | 1.3 | 60 |

-continued

| | LC-MS Method X018_S02 | | | |
|---|---|---|---|---|
| 1.00 | 0 | 100 | 1.3 | 60 |
| 1.10 | 0 | 100 | 1.3 | 60 |

Synthesis Methods

Method A

Synthesis of (1S,2S,4R)—N-[(1S)-1-cyano-2-[2-fluoro-4-[4-(oxetan-3-yl)piperazin-1-yl]phenyl]ethyl]-3-azabicyclo[2.2.1]heptane-2-carboxamide Example 1

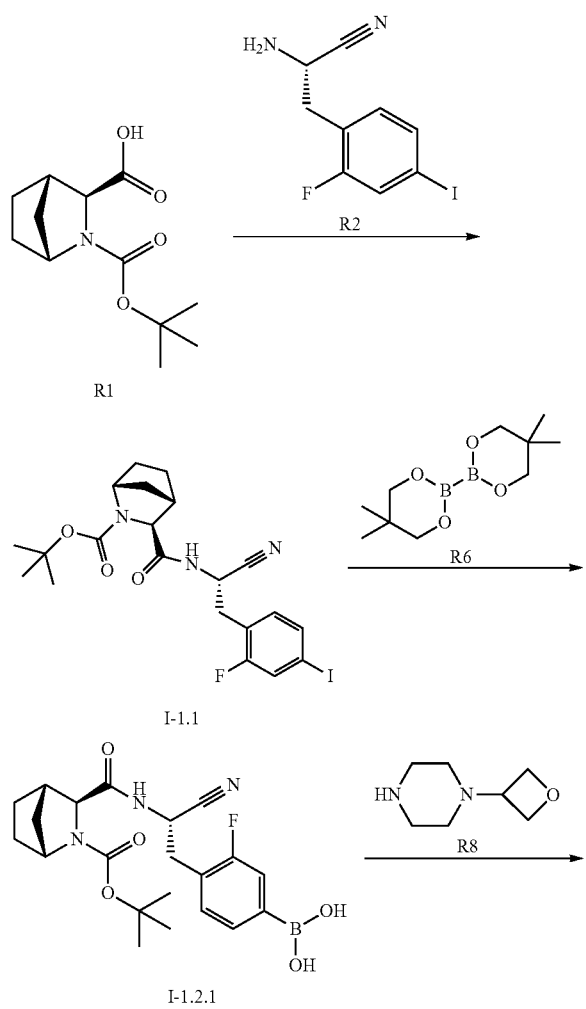

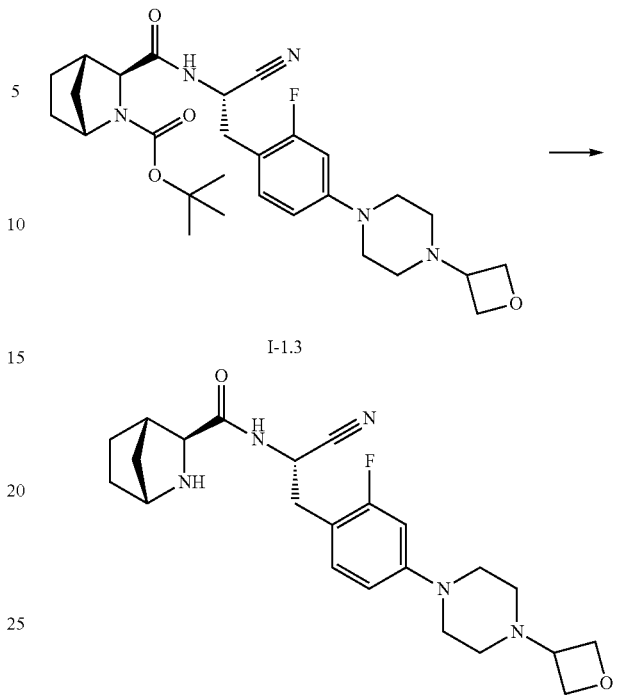

Example 1

Step 1: Synthesis of Intermediate I-1.1

To R1 (3.59 g, 14.88 mmol) are added DIPEA (6.4 mL, 37.44 mmol), HATU (6.22 g, 16.37 mmol) and DMF (10 mL) and stirred 1 h at r.t. A solution of R2 (4.32 g, 14.88 mmol) in DMF (10 ml) is added and stirred at r.t. The reaction mixture is diluted with dichloromethane (500 mL) and extracted with water, 1 mol/L hydrochloric acid, water, potassium carbonate solution (5%), water and brine. The organic layer is dried over MgSO$_4$ and concentrated in vacuo. The residue is triturated with acetonitrile and the precipitate is filtered off. The mother liquor is concentrated in vacuo, the residue is triturated with acetonitrile and the precipitate is filtered off. The isolated precipitates are combined.

Yield 69% m/z 514 [M+H]+, rt 1.31 min, LC-MS Method V011_S01

Step 2: Synthesis of Intermediate I-1.2.1

The reaction vessel is purged with argon. I-1.1 (4.5 g, 8.77 mmol), R6 (2.2 g, 9.74 mmol), potassium acetate (2.6 g, 26.49 mmol) and [1,1'-bis(diphenylphosphino)ferrocene]dichloropalladium(II), complex with dichloromethane (1:1) (145 mg, 0.18 mmol) are purged with argon. Dioxane (40 mL) is added and stirred 20 h at 80° C. The reaction mixture is diluted with dioxane, filtered through a pad of celite and the filtrate is concentrated in vacuo. The crude residue is dissolved in ethyl acetate and extracted with water and brine. The organic layer is dried and concentrated in vacuo. The residue is crystallized from acetonitrile to give I-1.2 as shown in table 1. Yield 49%.

TABLE 1

| Intermediate | Educt | Structure of Intermediate | m/z [M + H]+ | rt (min) | LC-MS method |
|---|---|---|---|---|---|
| I-1.2 | I-1.1 | | 432 (boronic acid) | 0.73 | V011_S01 |

The corresponding boronic acid is also isolated: The mother liquor from I-1.2 is concentrated and the residue is triturated with diethyl ether. The precipitate is filtered off. The mother liquor is worked up again as described above. The isolated precipitates are combined and purified by reversed phase HPLC to give I-1.2.1.

Yield 30% m/z 432 [M+H]+, rt 0.56 min, LC-MS Method X018_S01

Step 3: Synthesis of Intermediate I-1.3

To I-1.2.1 (130 mg, 0.30 mmol) in dichloromethane (4 mL) are added TEA (0.065 mL, 0.47 mmol), R8 (70 mg, 0.39 mmol), copper(II) acetate (82 mg, 0.45 mmol) and molecular sieve. The reaction mixture is stirred overnight at r.t. 7 N ammonia in methanol is added and concentrated in vacuo. The residue is purified by reversed phase HPLC.

Yield 34% m/z 528 [M+H]+, rt 1.11 min, LC-MS Method V101_S01.

The following intermediates as shown in Table 2 are synthesized in a similar fashion from the appropriate intermediates:

TABLE 2

| Intermediate | Educt | Structure of Intermediate | m/z [M + H]+ | rt (min) | LC-MS method |
|---|---|---|---|---|---|
| I-1.3.1 | I-1.2.1 | | 554 | 0.88 | X011_S03 |
| I-1.3.2 | I-1.2.1 | | 540 | 0.46 | X018_S01 |

Step 4: Synthesis of Example 1

To I-1.3 (54 mg, 0.10 mmol) in acetonitrile p-toluenesulfonic acid monohydrate (75 mg, 0.39 mmol) is added and stirred overnight at r.t. The reaction mixture is basified with ammonia and purified by reversed phase HPLC.

Yield 69% m/z 428 [M+H]+, rt 0.60 min, LC-MS Method 004_CA05.

Method A1

Synthesis of (1S,2S,4R)—N-[(1S)-1-cyano-2-[2-fluoro-4-[1-(oxetan-3-yl)-3,6-dihydro-2H-pyridin-4-yl]phenyl]ethyl]-3-azabicyclo[2.2.1]heptane-2-carboxamide

Example 4

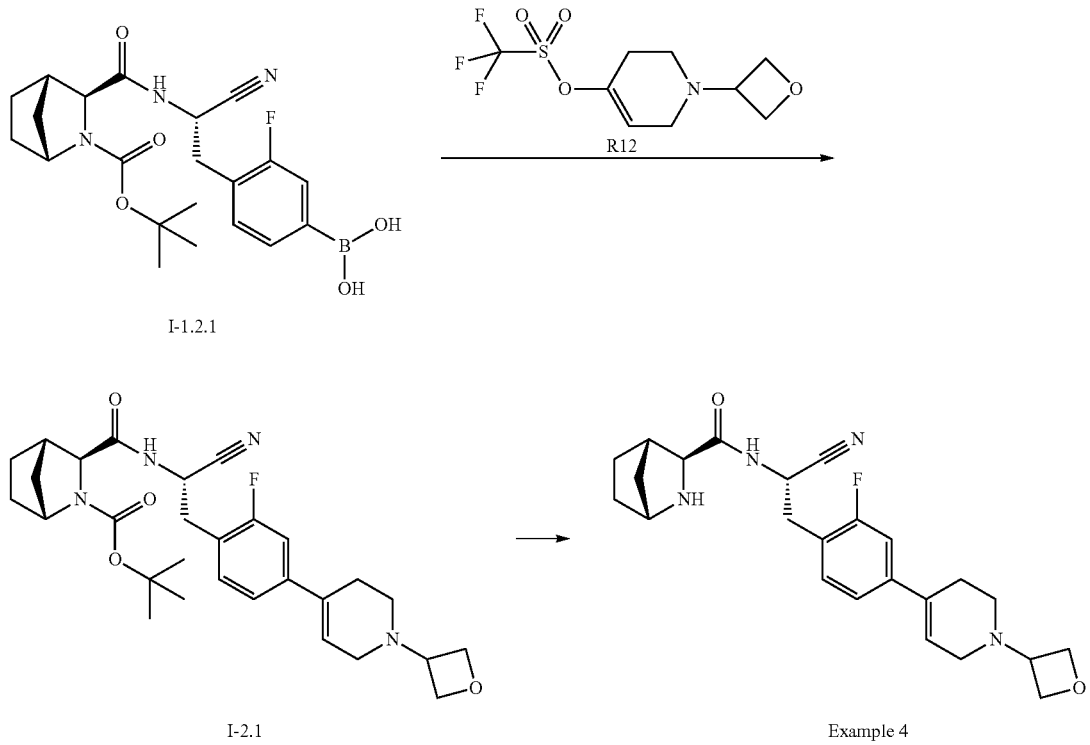

Step 1: Synthesis of Intermediate I-2.1

A mixture of I-1.2.1 (170 mg, 0.39 mmol), R12 (125 mg, 0.44 mmol), sodium carbonate solution (2 mol/L, 0.59 mL, 1.18 mmol), dioxane (5 mL) and 1,1'-Bis(diphenylphosphino)ferrocenedichloropalladium(II) (28.84 mg, 0.039 mmol) is purged with argon and stirred for 3 h at 80° C. The reaction mixture is diluted with ethyl acetate, filtered and washed with water. The aq. layer is extracted with ethyl acetate. The combined organic layers are dried and concentrated in vacuo. The crude residue is purified by reversed phase HPLC.

Yield 68% m/z 525 [M+H]+, rt 0.68 min, LC-MS Method X011_S03.

Step 2: Synthesis of Example 4

To I-2.1 (135 mg, 0.26 mmol) in acetonitrile p-toluenesulfonic acid monohydrate (150 mg, 0.79 mmol) is added and stirred overnight at r.t. The reaction mixture is basified with ammonia and purified by reversed phase HPLC.

Yield 95% m/z 425 [M+H]+, rt 0.58 min, LC-MS Method X011_S03.

Method B
Synthesis of (1S,2S,4R)—N-[(1S)-1-cyano-2-[2-fluoro-4-[5-(oxetan-3-yl)-1,3,3a,4,6,6a-hexahydro-pyrrolo[3,4-c]pyrrol-2-yl]phenyl]ethyl]-3-azabicyclo[2.2.1]heptane-2-carboxamide
Example 5
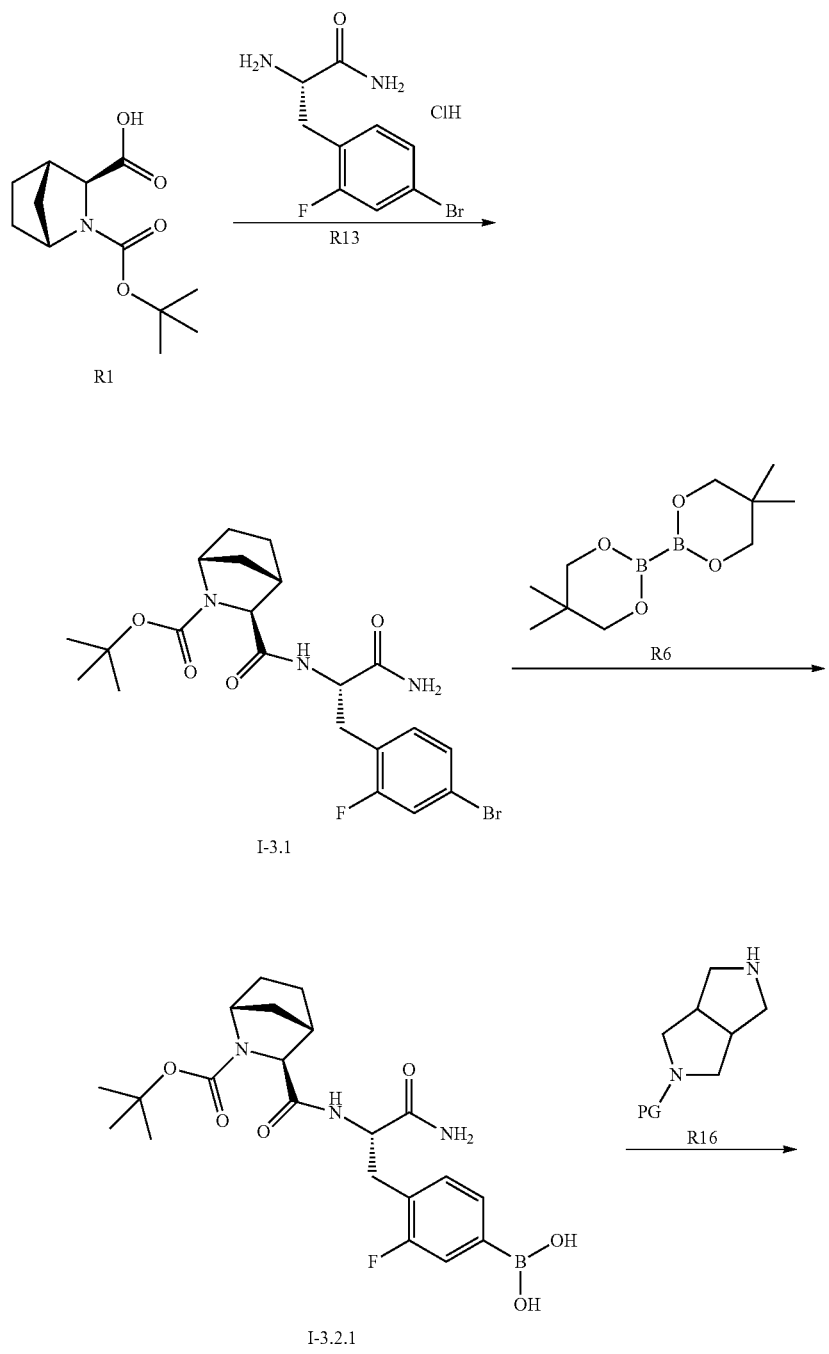

-continued
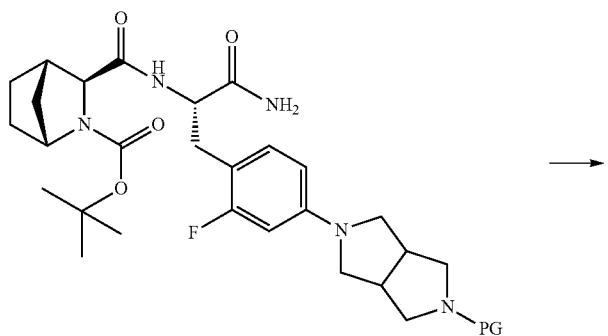
I-3.3
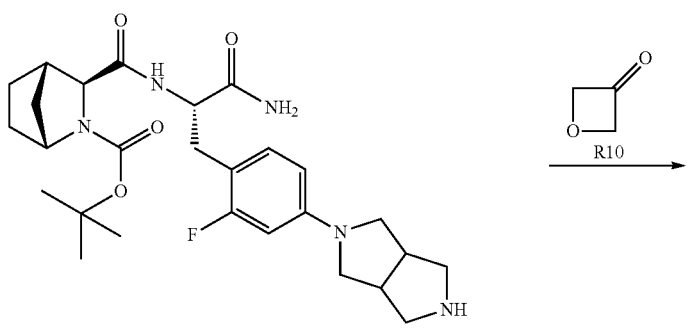
I-3.4
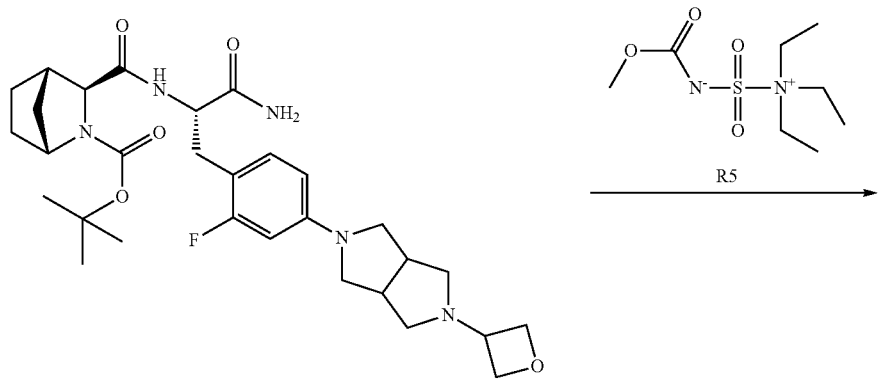
I-3.5
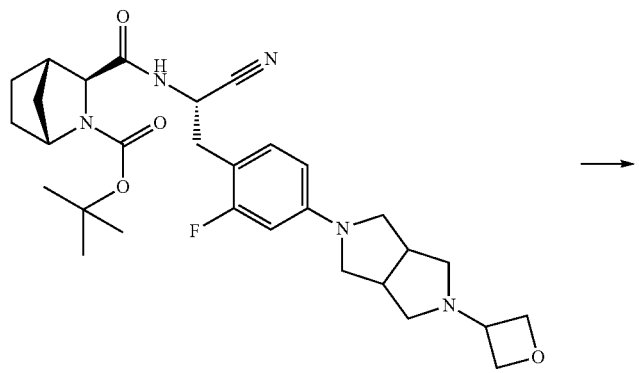
I-3.6

-continued

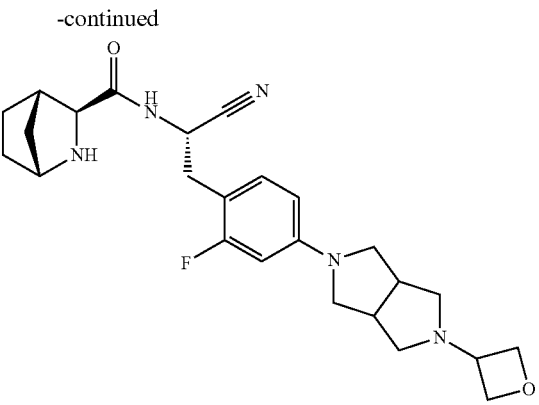

Example 5

PG means protecting group: either benzyl or benzylcarbamate.

Step 1: Synthesis of Intermediate I-3.1

To R13 (48.31 g, 200.30 mmol) in dichloromethane (695 mL) are added DIPEA (77.67 g, 600.90 mmol) and TBTU (70.74 g, 220.33 mmol) and stirred for 30 minutes at r.t. R1 (59.6 g, 200.30 mmol) is added and stirred 3 h at r.t. The reaction mixture is concentrated, dissolved in methyl-THF and extracted with 1 mol/L hydrochloric acid, 1 mol/L sodium hydroxide and brine. The organic layer is dried over MgSO4 and concentrated in vacuo.
Yield >95% m/z 484 [M+H]+

Step 2: Synthesis of Intermediate I-3.2.1

The reaction vessel is purged with argon. I-3.1 (12.0 g, 24.78 mmol), R6 (6.72 g, 29.73 mmol), potassium acetate (7.3 g, 74.33 mmol) and [1,1'-bis(diphenylphosphino)ferrocene]dichloropalladium(II), complex with dichloromethane (1:1) (809.29 mg, 0.99 mmol) in dioxane (100 mL) are stirred together 20 h at 80° C. The reaction mixture is diluted with ethyl acetate and halfsaturated sodium chloride solution. The aq. layer is washed with ethyl acetate and the combined organic layers are dried over MgSO$_4$ and concentrated in vacuo. The crude residue is diluted with acetonitrile (20 mL) and left over two days at r.t., concentrated and recrystallized from diethyl ether to give I-3.2 as shown in table 3.
Yield 74%.

TABLE 3

| Intermediate | Educt | Structure of Intermediate | m/z [M + H]+ | rt (min) | LC-MS method |
|---|---|---|---|---|---|
| I-3.2 | I-3.1 | | 450 (boronic acid) | 0.67 | V011_S01 |

The corresponding boronic acid is also isolated: The mother liquor from I-3.2 is concentrated and the residue purified by reversed phase HPLC to give I-3.2.1.
Yield 20% m/z 450 [M+H]+, rt 0.65 min, LC-MS Method V101_S01

Step 3: Synthesis of Intermediate I-3.3

To I-3.2.1 (1.5 g, 3.34 mmol) in dichloromethane (70 mL) are added TEA (0.74 mL, 5.34 mmol), R16 (0.99 g, 4.01 mmol), copper(II) acetate (970.27 mg, 5.34 mmol) and molecular sieve. The reaction mixture is stirred over 2 days at r t Ammonia is added and the organic layer is concentrated in vacuo. The residue is purified by reversed phase HPLC.

Yield 18% m/z 650 [M+H]+, rt 0.77 min, LC-MS Method X018_S02.

The following intermediates as shown in Table 4 are synthesized in a similar fashion from the appropriate intermediates:

TABLE 4

| Intermediate | Educt | Structure of Intermediate | m/z [M + H]+ | rt (min) | LC-MS method |
|---|---|---|---|---|---|
| I-3.3.1 | I-3.2 | 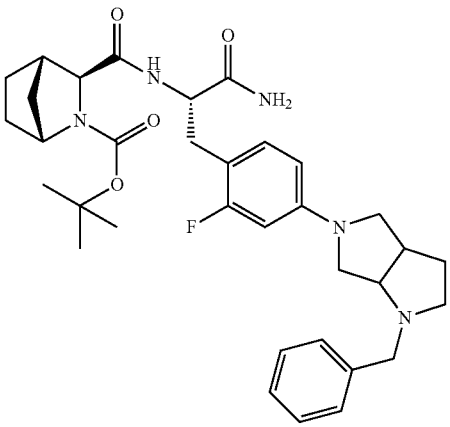 [SMILES: CC(C)(C)OC(=O)N1[C@@H]2CC[C@@H](C2)[C@H]1C(=O)N[C@@H](Cc1ccc(N2CC3CCN(Cc4ccccc4)C3C2)cc1F)C(N)=O] | 606 | 1.40 | V011_S01 |
| I-3.3.2 | I-3.2 | 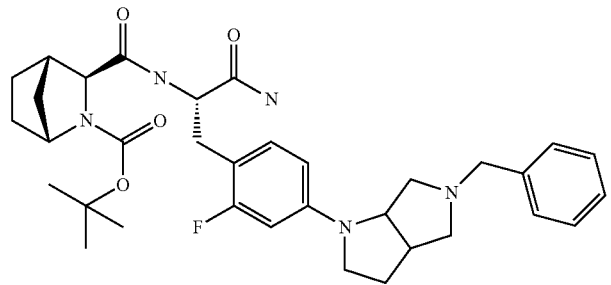 [SMILES: CC(C)(C)OC(=O)N1[C@@H]2CC[C@@H](C2)[C@H]1C(=O)N[C@@H](Cc1ccc(N2CCC3CN(Cc4ccccc4)CC32)cc1F)C(N)=O] | 606 | 1.38 | V011_S01 |
| I-3.3.3 | I-3.2 | 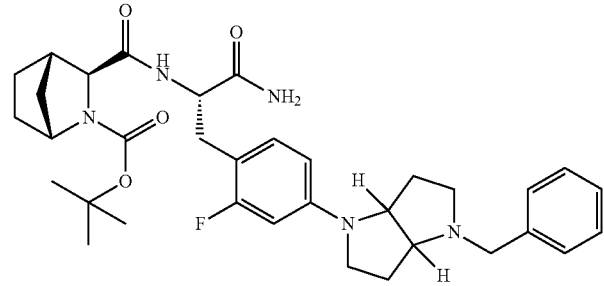 Mixture of trans isomers | 606 | 1.33 | V011_S01 |
| I-3.3.4 | I-3.2.1 | 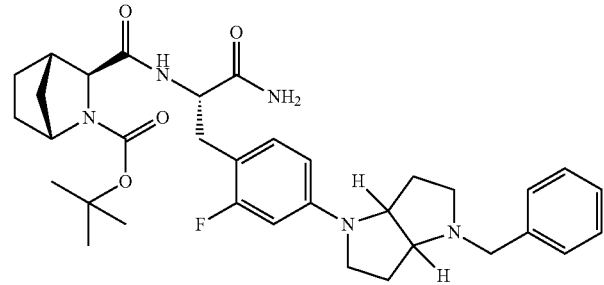 Mixture of cis isomers | 606 | 1.40 | V011_S01 |

Step 4: Synthesis of Intermediate I-3.4

For PG=benzylcarbamate:

To I-3.3 (390 mg, 0.60 mmol) in ethyl acetate (20 mL) and methanol (10 mL) is added Pd/C 10% (50 mg) and stirred under hydrogen (50 psi) for 5.5 h at r.t. The reaction mixture is filtered and the filtrate is concentrated in vacuo.

Yield 99% m/z 516 [M+H]+, rt 0.43 min, LC-MS Method X018_S02.

For PG=benzyl (e.g. I-3.4.1)

The reaction conditions differ: solvent is methanol, reaction time is 29 h at r.t. and the crude residue is purified by reversed phase HPLC.

The following intermediates as shown in Table 5 are synthesized in a similar fashion from the appropriate intermediates:

TABLE 5

| Intermediate | Educt | Structure of Intermediate | m/z [M + H]+ | rt (min) | LC-MS method |
|---|---|---|---|---|---|
| I-3.4.1 | I-3.3.1 | 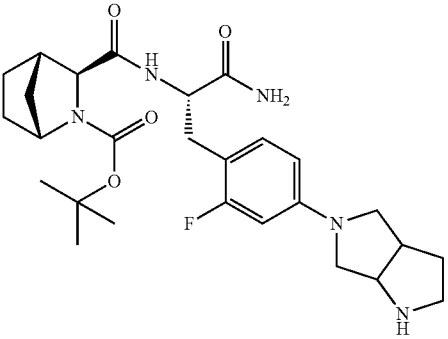 [SMILES: CC(C)(C)OC(=O)N1[C@@H]2CC[C@@H](C2)[C@H]1C(=O)N[C@@H](Cc1ccc(N2CC3CCNC3C2)cc1F)C(N)=O] | 516 | 1.02 | V011_S01 |
| I-3.4.2 | I-3.3.2 | 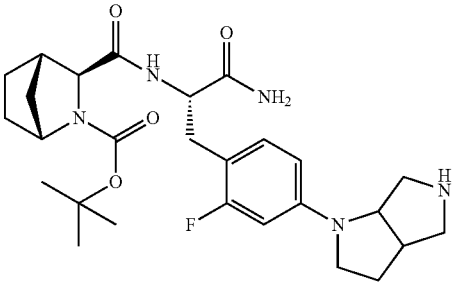 [SMILES: CC(C)(C)OC(=O)N1[C@@H]2CC[C@@H](C2)[C@H]1C(=O)N[C@@H](Cc1ccc(N2CCC3CNCC32)cc1F)C(N)=O] | 516 | 1.00 | V011_S01 |
| I-3.4.3 | I-3.3.3 | 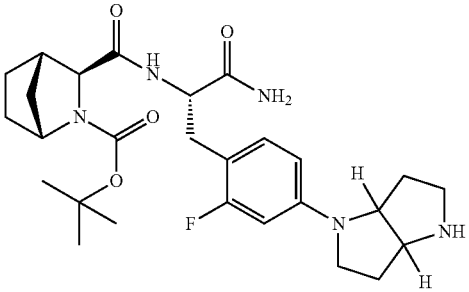 [SMILES: CC(C)(C)OC(=O)N1[C@@H]2CC[C@@H](C2)[C@H]1C(=O)N[C@@H](Cc1ccc(N2CCC3NCCC32)cc1F)C(N)=O] Mixture of trans isomers | 516 | 0.97 | V011_S01 |
| I-3.4.4 | I-3.3.4 | 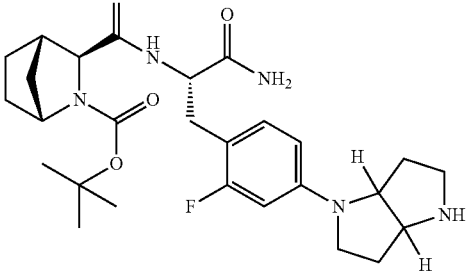 Mixture of cis isomers | 516 | 0.98 | V011_S01 |

Step 5: Synthesis of Intermediate I-3.5

To I-3.4 (60 mg, 0.12 mmol) in dichloromethane are added R10 (10.84 µl, 0.16 mmol) and acetic acid (6.66 µl, 0.12 mmol) and stirred for 1 h at r.t. Sodium triacetoxyborohydride (46.73 mg, 0.21 mmol) is added and stirred overnight at r.t. The reaction mixture is diluted with dichloromethane and saturated sodium hydrogencarbonate solution. The organic layer is dried and concentrated in vacuo.

Yield >95% m/z 572 [M+H]+, rt 1.02 min, LC-MS Method V011_S01.

The following intermediates as shown in Table 6 are synthesized in a similar fashion from the appropriate intermediates:

TABLE 6

| Intermediate | Educt | Structure of Intermediate | m/z [M + H]+ | rt (min) | LC-MS method |
|---|---|---|---|---|---|
| I-3.5.1 | I-3.4.1 | 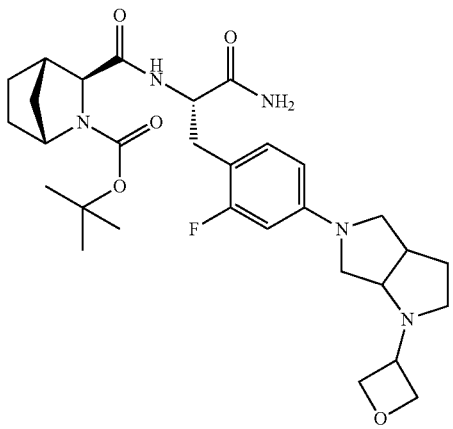 [SMILES: CC(C)(C)OC(=O)N1[C@@H]2CC[C@@H](C2)[C@H]1C(=O)N[C@@H](Cc1ccc(N2CC3CCN(C4COC4)C3C2)cc1F)C(N)=O] | 572 | 1.05 | V011_S01 |
| I-3.5.2 | I-3.4.2 | 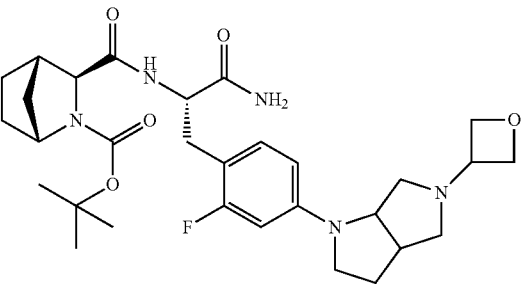 [SMILES: CC(C)(C)OC(=O)N1[C@@H]2CC[C@@H](C2)[C@H]1C(=O)N[C@@H](Cc1ccc(N2CCC3CN(C4COC4)CC32)cc1F)C(N)=O] | 572 | 1.05 | V011_S01 |
| I-3.5.3 | I-3.4.3 | 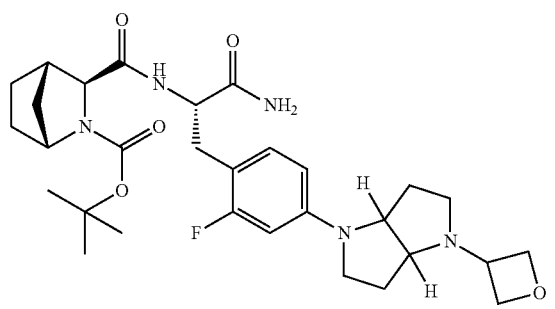 [SMILES: CC(C)(C)OC(=O)N1[C@@H]2CC[C@@H](C2)[C@H]1C(=O)N[C@@H](Cc1ccc(N2CCC3C2CCN3C2COC2)cc1F)C(N)=O] Mixture of trans isomers | 572 | 1.00 | V011_S01 |

TABLE 6-continued

| Inter-mediate | Educt | Structure of Intermediate | m/z [M + H]+ | rt (min) | LC-MS method |
|---|---|---|---|---|---|
| I-3.5.4 | I-3.4.4 | *(structure shown)* Mixture of cis isomers | 572 | 1.03 | V011_S01 |

Step 6: Synthesis of I-3.6

To I-3.5 (67 mg, 0.12 mmol) in dichloromethane (7 mL) is added R5 (69.82 mg, 0.29 mmol) and stirred overnight at r.t. The reaction mixture is concentrated in vacuo and purified by reversed phase HPLC.

Yield 69% m/z 554 [M+H]+, rt 1.14 min, LC-MS Method V011_S01.

The following intermediates as shown in Table 7 are synthesized in a similar fashion from the appropriate intermediates:

TABLE 7

| Inter-mediate | Educt | Structure of Intermediate | m/z [M + H]+ | rt (min) | LC-MS method |
|---|---|---|---|---|---|
| I-3.6.1 | I-3.5.1 | *(structure shown)* | 554 | 1.17 | V011_S01 |
| I-3.6.2 | I-3.5.2 | *(structure shown)* | 554 | 1.19 | V011_S01 |

TABLE 7-continued

| Intermediate | Educt | Structure of Intermediate | m/z [M + H]+ | rt (min) | LC-MS method |
|---|---|---|---|---|---|
| I-3.6.3 | I-3.5.3 | 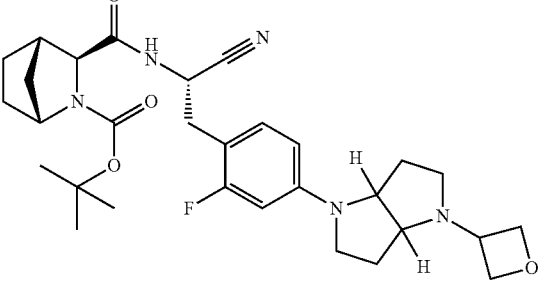<br>Mixture of trans isomers | 554 | 1.13 | V011_S01 |
| I-3.6.4 | I-3.5.4 | 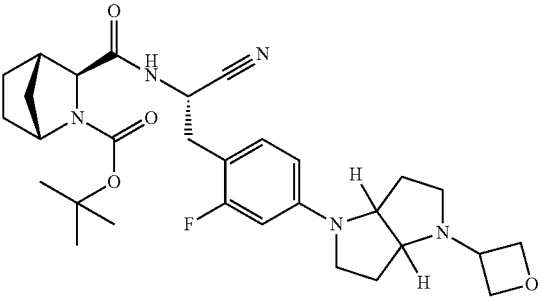 [SMILES: CC(C)(C)OC(=O)N1[C@@H]2CC[C@@H](C2)[C@H]1C(=O)N[C@H](C#N)Cc1ccc(N2CCC3C2CCN3C2COC2)cc1F]<br>Mixture of cis isomers | 554 | 1.16 | V011_S01 |

Step 7: Synthesis of Example 5

To I-3.6 (45 mg, 0.08 mmol) in acetonitrile (3 mL) p-toluenesulfonic acid monohydrate (54.11 mg, 0.28 mmol) is added and stirred overnight at r.t. The reaction mixture is basified with ammonia (25%) and purified by reversed phase HPLC.

Yield 48% m/z 454 [M+H]+, rt 0.76 min, LC-MS Method 003_CA04

Method B1

Synthesis of (1S,2S,4R)—N-[(1S)-1-cyano-2-[2-fluoro-4-[1-(oxetan-3-yl)-4-piperidyl]phenyl]ethyl]-3-azabicyclo[2.2.1]heptane-2-carboxamide Example 10

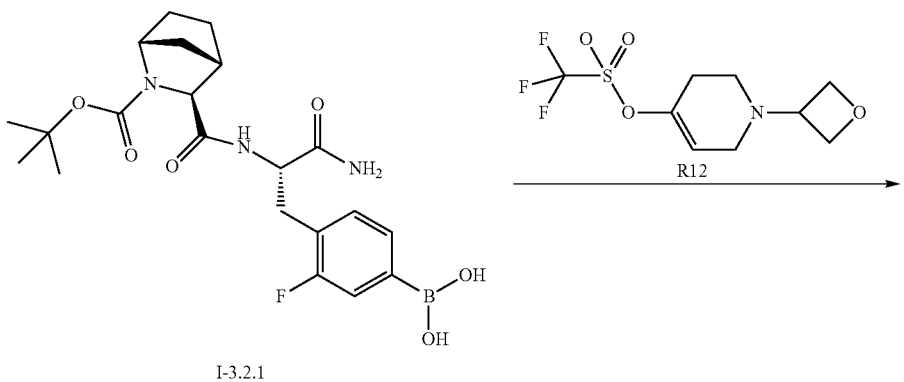

I-3.2.1

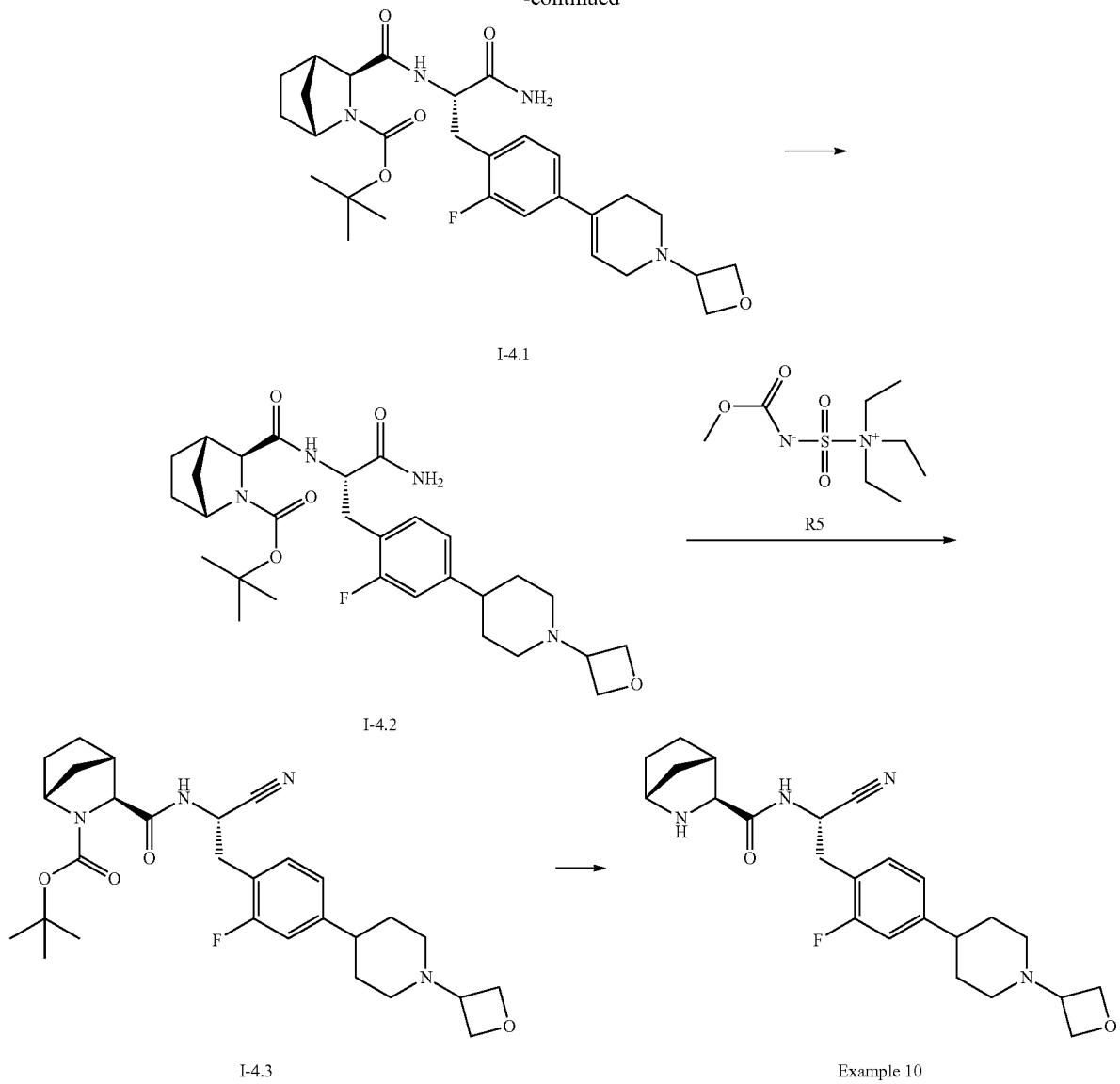

Step 1: Synthesis of Intermediate I-4.1

A mixture of I-3.2.1 (500 mg, 1.11 mmol), R12 (350 mg, 1.22 mmol), sodium carbonate solution (2 mol/L, 1.67 mL, 3.34 mmol), dioxane (10 mL) and 1,1'-Bis(diphenylphosphino)ferrocenedichloropalladium(II) (81.43 mg, 0.11 mmol) is purged with argon and stirred for 3 h at 80° C. The reaction mixture is diluted with ethyl acetate, filtered and washed with water. The aq. layer is extracted with ethyl acetate. The combined organic layers are dried and concentrated in vacuo. The crude residue is purified by reversed phase HPLC.

Yield 63% m/z 543 M+H+, rt 0.60 min, LC-MS Method X011_S03.

Step 2: Synthesis of intermediate I-4.2

To I-4.1 (375 mg, 0.69 mmol) in methanol (25 mL) is added Pd/C (100 mg) and stirred under hydrogen (50 psi) for 4 h at 50° C. The reaction mixture is filtered and the filtrate is concentrated in vacuo.

Yield 98% m/z 545 [M+H]+, rt 0.60 min, LC-MS Method X011_S03.

Step 3: Synthesis of intermediate I-4.3

To I-4.2 (375 mg, 0.69 mmol) in dichloromethane (25 mL) is added R5 (260 mg, 1.09 mmol) and stirred overnight at r.t. The reaction mixture is diluted with dichloromethane and extracted with water. The organic layer is dried, concentrated in vacuo and purified by reversed phase HPLC.

Yield 85% m/z 527 [M+H]+, rt 0.68 min, LC-MS Method X011_S03.

Step 4: Synthesis of example 10

To I-4.3 (300 mg, 0.57 mmol) in acetonitrile p-toluenesulfonic acid monohydrate (330 mg, 1.74 mmol) is added and stirred 1.5 h at 50° C. The reaction mixture is basified with ammonia and purified by reversed phase HPLC.

Yield 77% m/z 427 [M+H]+, rt 0.61 min, LC-MS Method X011_S03.

Method B2
Synthesis of Example 11
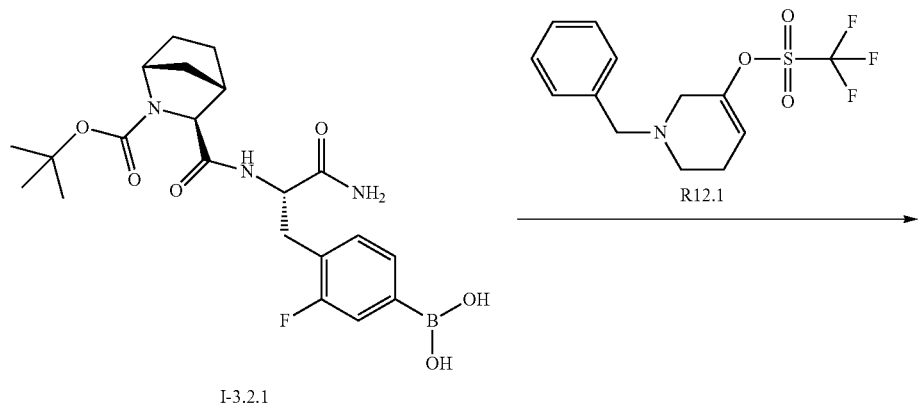
I-3.2.1
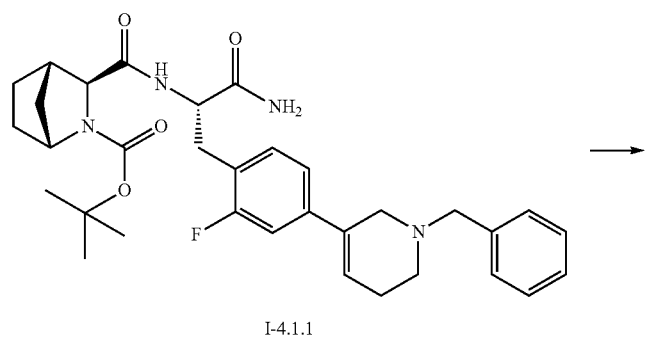
I-4.1.1
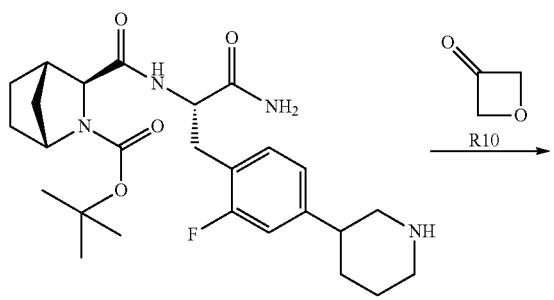
I-4.2.1
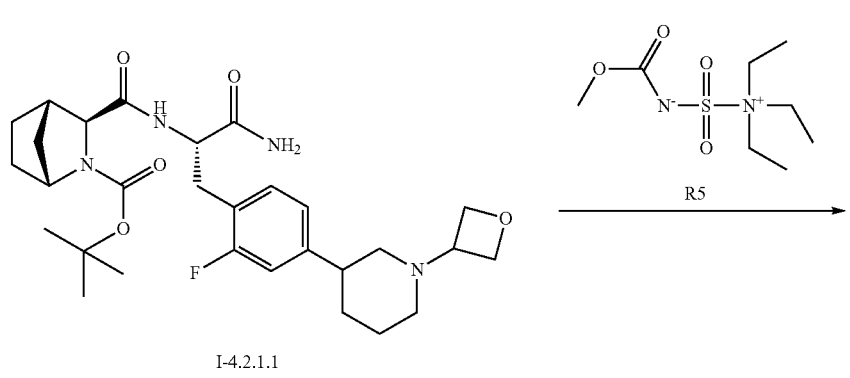
I-4.2.1.1

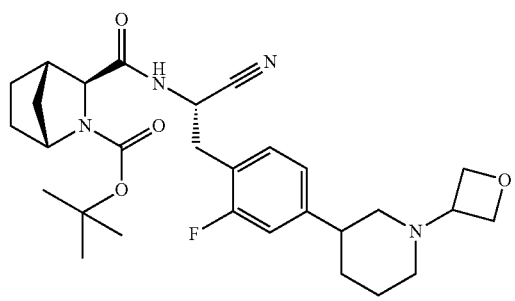

I-4.3.1

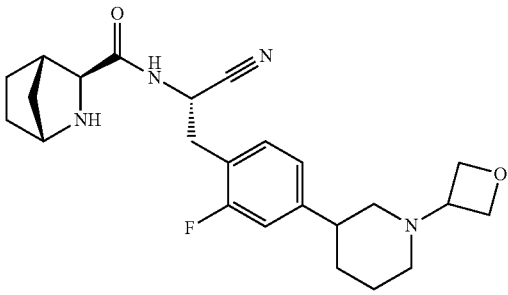

Example 11

Step 1: Synthesis of Intermediate I-4.1.1

The reaction is carried out under argon atmosphere.

A mixture of I-3.2.1 (1.0 g, 2.23 mmol), R12.1 (795 mg, 2.47 mmol), sodium carbonate solution (2 mol/L, 2.23 mL, 4.45 mmol), dioxane (20 mL) and 1,1'-Bis(diphenylphosphino)ferrocenedichloropalladium(II) (162.86 mg, 0.22 mmol) is stirred for 30 minutes at 80° C. The reaction mixture is diluted with ethyl acetate and water. The aq. layer is extracted with ethyl acetate. The combined organic layers are dried over $MgSO_4$ and concentrated in vacuo. The crude residue is purified by reversed phase HPLC.

Yield 46% m/z 577 [M+H]+, rt 0.50 min, LC-MS Method X018_S02.

The following intermediates as shown in Table 8 are synthesized in a similar fashion from the appropriate intermediates:

TABLE 8

| Intermediate | Educt | Structure of Intermediate | m/z [M + H]+ | rt (min) | LC-MS method |
|---|---|---|---|---|---|
| I-4.1.2 | I-3.2.1 | | 563 | 0.50 | X018_S02 |
| I-4.1.3 | I-3.2 | Mixture of cis isomers | 603 | 1.40 | V011_S01 |

Step 2: Synthesis of intermediate I-4.2.1

To I-4.1.1 (550 mg, 0.95 mmol) in methanol (10 mL) is added Pd/C 10% (60 mg) and stirred under hydrogen (50 psi) for 44 h at r.t. and for 6 h at 50° C. The reaction mixture is filtered and the filtrate is concentrated in vacuo.

Yield 91% m/z 489 [M+H]+, rt 0.44 min, LC-MS Method X018_S02.

The following intermediates as shown in Table 9 are synthesized in a similar fashion from the appropriate intermediates:

TABLE 9

| Intermediate | Educt | Structure of Intermediate | m/z [M + H]+ | rt (min) | LC-MS method |
|---|---|---|---|---|---|
| I-4.2.2 | I-4.1.2 | 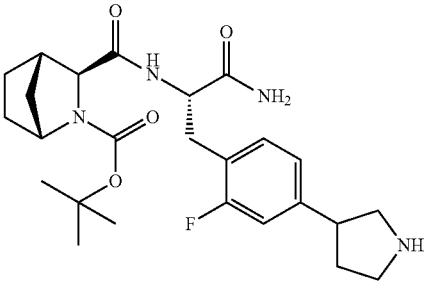 [SMILES: CC(C)(C)OC(=O)N1[C@@H]2CC[C@@H](C2)[C@H]1C(=O)N[C@@H](Cc1ccc(C2CCNC2)cc1F)C(N)=O] | 475 | 0.41 | X018_S02 |
| I-4.2.3 | I-4.1.3 | 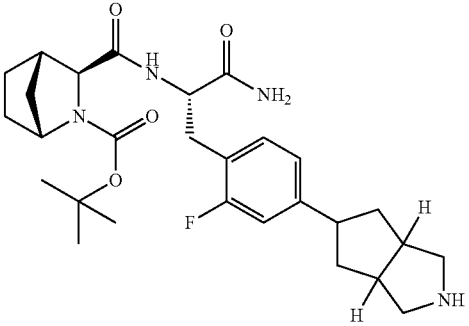 [SMILES: CC(C)(C)OC(=O)N1[C@@H]2CC[C@@H](C2)[C@H]1C(=O)N[C@@H](Cc1ccc(C2CC3CNCC3C2)cc1F)C(N)=O] Mixture of all-cis isomer and trans-cis-cis isomer | 515 | 1.13 | V011_S01 |

The reaction conditions for I-4.2.2 differ: reaction time is ~40 h at r.t., ~8 h at 50° C. and ~40 h at 70° C.
The reaction conditions for I-4.2.3 differ: the reaction is carried out at r.t.

Step 3: Synthesis of Intermediate I-4.2.1.1

To I-4.2.1 (110 mg, 0.23 mmol) in dichloromethane are added R10 (24.34 mg, 0.34 mmol) and acetic acid (12.88 µl, 0.23 mmol) and stirred for 1 h at r.t. Sodium triacetoxyborohydride (85.39 mg, 0.38 mmol) is added and stirred overnight at r.t. The reaction mixture is diluted with dichloromethane and saturated sodium hydrogencarbonate solution. The organic layer is dried and concentrated in vacuo.

Yield 99% m/z 545 [M+H]+, rt 0.43 min, LC-MS Method X018_502.

The following intermediates as shown in Table 10 are synthesized in a similar fashion from the appropriate intermediates:

TABLE 10

| Intermediate | Educt | Structure of Intermediate | m/z [M + H]+ | rt (min) | LC-MS method |
|---|---|---|---|---|---|
| I-4.2.2.1 | I-4.2.2 | 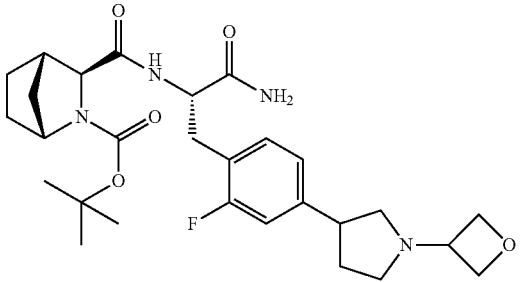 [SMILES: CC(C)(C)OC(=O)N1[C@@H]2CC[C@@H](C2)[C@H]1C(=O)N[C@@H](Cc1ccc(C2CCN(C3COC3)C2)cc1F)C(N)=O] | 531 | 0.98 | V011_S01 |

TABLE 10-continued

| Intermediate | Educt | Structure of Intermediate | m/z [M + H]+ | rt (min) | LC-MS method |
|---|---|---|---|---|---|
| I-4.2.3.1 | I-4.2.3 | 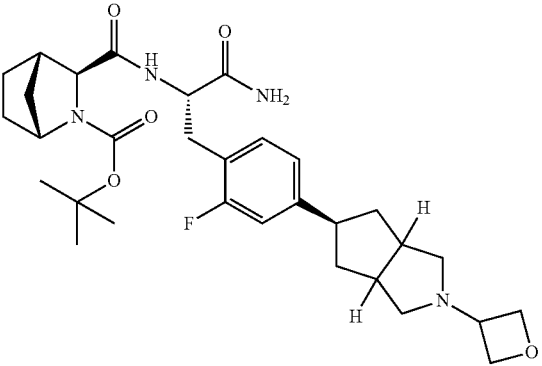 mixture of cis isomers | 571 | 1.04 | V011_S01 |
| I-4.2.3.2 | I-4.2.3 | 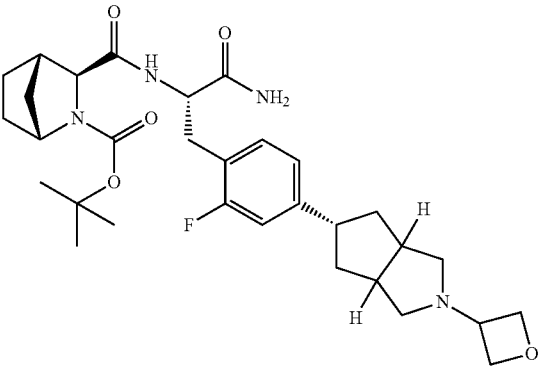 mixture of cis isomers | 571 | 1.12 | V011_S01 |

Step 4: Synthesis of intermediate I-4.3.1

To I-4.2.1.1 (135 mg, 0.25 mmol) in dichloromethane (7 mL) is added R5 (147.67 mg, 0.62 mmol) and stirred overnight at r.t. The reaction mixture is concentrated in vacuo and purified by reversed phase HPLC.

Yield 46% m/z 527 [M+H]+, rt 0.48 min, LC-MS Method X018_S02.

The following intermediates as shown in Table 11 are synthesized in a similar fashion from the appropriate intermediates:

TABLE 11

| Intermediate | Educt | Structure of Intermediate | m/z [M + H]+ | rt (min) | LC-MS method |
|---|---|---|---|---|---|
| I-4.3.2 | I-4.2.2.1 | 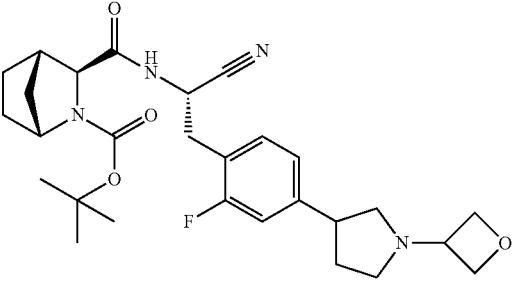 [SMILES: CC(C)(C)OC(=O)N1[C@@H]2CC[C@@H](C2)[C@H]1C(=O)N[C@H](C#N)Cc1ccc(C2CCN(C3COC3)C2)cc1F] | 513 | 1.10 | V011_S01 |

TABLE 11-continued

| Intermediate | Educt | Structure of Intermediate | m/z [M + H]+ | rt (min) | LC-MS method |
|---|---|---|---|---|---|
| I-4.3.3 | I-4.2.3.1 | mixture of cis isomers | 553 | 1.17 | V011_S01 |
| I-4.3.4 | I-4.2.3.2 | mixture of cis isomers | 553 | 1.24 | V011_S01 |

Step 4: Synthesis of Example 11

To I-4.3.1 (60 mg, 0.11 mmol) in acetonitrile (3 mL) p-toluenesulfonic acid monohydrate (75.85 mg, 0.40 mmol) is added and stirred overnight at r.t. The reaction mixture is basified with ammonia (25%) and purified by reversed phase HPLC.

Yield 68% m/z 427 [M+H]+, rt 0.67 min, LC-MS Method 004_CA05

Method C

Synthesis of N-[(1S)-1-cyano-2-[2-fluoro-4-[4-(oxetan-3-yl)piperazin-1-yl]phenyl]ethyl]-2-azabicyclo[2.2.2]octane-1-carboxamide Example 15

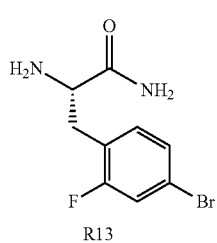

R13

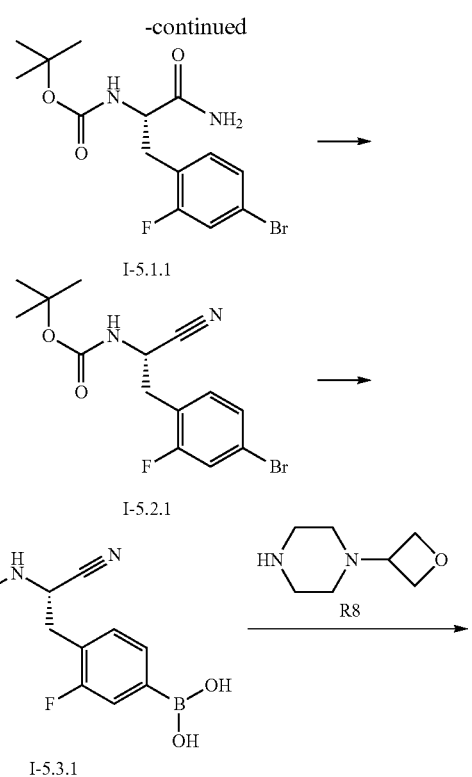

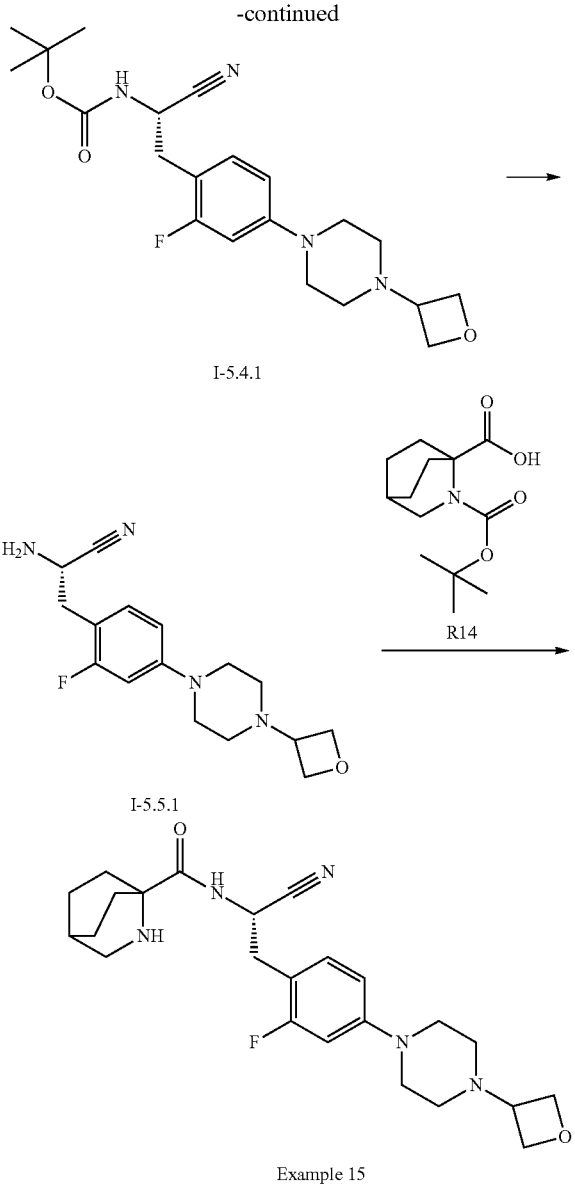

Step 1: Synthesis of Intermediate I-5.1.1

To R13 (1.0 g, 3.36 mmol) are added DIPEA (0.6 mL, 3.36 mmol), R4 (1.1 g, 5.04 mmol) and dichloromethane (15 mL) and stirred 8 h at r.t. The solvent is removed in vacuo. Diethylether is added and the mixture is washed with 15 mL HCl (0.5 mol/L), stirred 10 min at 40° C., cooled to r.t. and the precipitate is filtered off.

Yield 85% m/z 361/363 [M+H]+

Step 2: Synthesis of Intermediate I-5.2.1

To I-5.1.1 (1.0 g, 2.85 mmol) in dichloromethane (25 mL) is added R5 (1.4 g, 5.74 mmol) and stirred overnight at r.t. The reaction mixture is concentrated in vacuo and purified by reversed phase HPLC.

Yield 97% m/z 341/342 [M+H]+, rt 0.70 min, LC-MS Method X011_S03.

Step 3: Synthesis of Intermediate I-5.3.1

The reaction vessel is purged with argon. I-5.2.1 (3.0 g, 8.74 mmol), R6 (2.2 g, 9.74 mmol), potassium acetate (2.6 g, 26.49 mmol) and [1,1'-bis(diphenylphosphino)ferrocene]dichloropalladium(II), complex with dichloromethane (1:1) (143 mg, 0.18 mmol) are purged with argon. Dioxane (150 mL) is added and stirred 16 h at 80° C. The reaction mixture is diluted with dioxane, filtered through a pad of celite and the filtrate is concentrated in vacuo. The crude residue is dissolved in ethyl acetate and extracted with water and brine. The organic layer is dried and concentrated in vacuo. The residue is and purified by reversed phase HPLC.

Yield 79% m/z 309 [M+H]+, rt 0.48 min, LC-MS Method X012_S01.

Step 4: Synthesis of Intermediate I-5.4.1

To I-5.3.1 (125 mg, 0.40 mmol) in dichloromethane (15 mL) are added TEA (0.08 mL, 0.57 mmol), R8 (67 mg, 0.47 mmol), copper(II) acetate (105 mg, 0.58 mmol) and molecular sieve. The reaction mixture is stirred overnight at r.t. 7 N ammonia in methanol is added and concentrated in vacuo. The residue is purified by reversed phase HPLC.

Yield 16% m/z 405 [M+H]+, rt 0.58 min, LC-MS Method X011_S03.

The following intermediates as shown in Table 12 are synthesized in a similar fashion from the appropriate intermediates:

TABLE 12

| Intermediate | Educt | Structure of Intermediate | m/z [M + H]+ | rt (min) | LC-MS method |
|---|---|---|---|---|---|
| I-5.4.2 | I-5.3.1 | | 431 | 1.12 | V011_S01 |

Step 5: Synthesis of Intermediate I-5.5.1

To I-5.4.1 (27 mg, 0.07 mmol) in acetonitrile p-toluenesulfonic acid monohydrate (50 mg, 0.26 mmol) is added and stirred overnight at r.t. The reaction mixture is basified with ammonia and purified by reversed phase HPLC.

Yield 49% m/z 305 [M+H]+, rt 0.37 min, LC-MS Method X011_S03

The following intermediates as shown in Table 13 are synthesized in a similar fashion from the appropriate intermediates:

TABLE 13

| Intermediate | Educt | Structure of Intermediate | m/z [M + H]+ | rt (min) | LC-MS method |
|---|---|---|---|---|---|
| I-5.5.2 | I-5.4.2 | 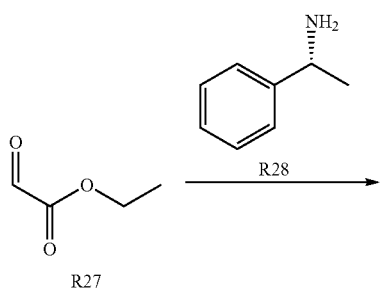 | 331 | 0.85 | V011_S01 |

Step 6: Synthesis of Example 15

To R14 (88 mg, 0.34 mmol) are added dichloromethane (2 mL), N-methyl-morpholine (126 µL, 1.10 mmol). The mixture is cooled to 0° C., I-5.5.1 (70 mg, 0.23 mmol) and PPA (268 µL, 50% in DMF) is added and stirred 17 h at 50° C. The reaction mixture is concentrated in vacuo and purified by reversed phase HPLC.

Yield 64% m/z 442 [M+H]+, rt 0.51 min, LC-MS Method X011_S03.

Synthesis of Starting Materials/Educts

Synthesis of (1S,2S,4R)-3-[(tert.-butoxy)carbonyl]-3-azabicyclo[2.2.1]heptane-2-carboxylate (R1)

The compound is commercially available or can be synthesized in analogy to Tararov et al, Tetrahedron Asymmetry 13 (2002), 25-28.

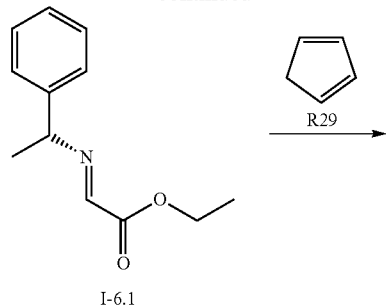

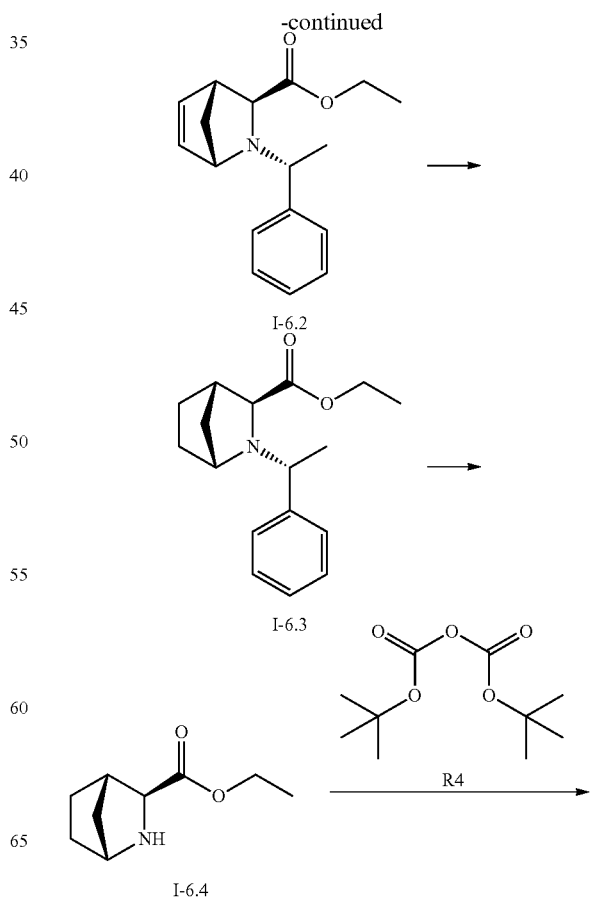

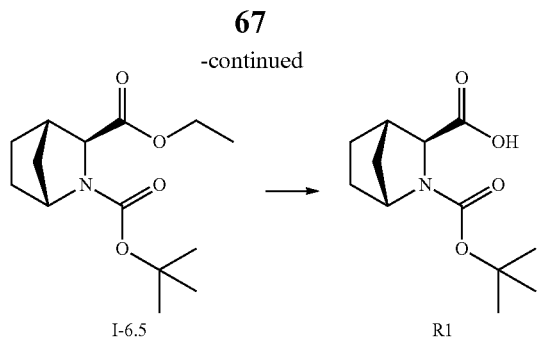

Step 1: Synthesis of I-6.1

To a solution of R27 (100 g, 48.98 mmol), from a commercially available solution in toluene (50%) in toluene (200 ml) is added R28 (59.35 g, 48.98 mmol) dropwise at r.t. and subsequently rinsed with toluene (200 mL). The reaction mixture is concentrated in vacuo at 50° C. bath temperature. The product is used without further purification.
Yield >95% m/z 206 [M+H]+

Step 2: Synthesis of I-6.2

A solution of I-6.1 (194 g, 945.18 mmol) in dichloromethane (1800 mL) is cooled down to −16° C. TFA (73 mL, 945.18 mmol) is added dropwise. R29 (68.73 g, 1.04 mol) (freshly distilled from dicyclopentadien) is added dropwise at ~−30° C. The reaction mixture is stirred for 1 h at −35° C.--40° C. and at r.t. overnight. The mixture is slowly poured into a solution of sodiumhydrogen carbonate (200 g) in water (2 L) and stirred for 1 h at r.t. The organic layer is washed with half saturated sodium hydrogen carbonate solution, dried over Na₂SO₄ and concentrated in vacuo.
Yield 87% m/z 272 [M+H]+

Step 3: Synthesis of I-6.3

To a solution of I-6.2 (220 g, 810.75 mmol) in isopropanol (1100 mL), Raney-nickel is added (22 g) and reacted at 50 psi under a hydrogen atmosphere at room temperature for ~3 h. The catalyst is filtered off, the solution is concentrated in vacuo and the residue is triturated with a solution of hydrochloric acid in ethanol 10 mol/L (90 mL) and TBME. The precipitate is filtered off and dried. The product is recrystallized from isopropanol and TBME
Yield 41% m/z 274 [M+H]+

Step 4: Synthesis of I-6.4

To a solution of I-6.3 (100 g, 322.76 mmol) in ethanol (1000 mL), 10% Pd/C is added (10 g) and reacted at 50 bar under a hydrogen atmosphere at room temperature. The catalyst is filtered off, the solution concentrated in vacuo.
Yield >95% m/z 170 [M+H]+

Step 5: Synthesis of I-6.5

To I-6.4 (69 g, 335.47 mmol) in THF (500 mL) are added triethylamin (119.16 ml, 848.74 mmol), and water (10 mL). R4 (76.88 g, 352.24 mmol) is added and the resulting mixture stirred for 46 hours at room temperature, then concentrated in vacuo. Toluene is added to the residue, subsequently extracted with water, 1 N KHSO₄ solution and water, before the organic layer is concentrated in vacuo.
Yield >95% m/z 270 [M+H]+

Step 6: Synthesis of R1

A mixture of I-6.5 (95 g, 352.72 mmol) in acetone (500 ml), water (280 ml) and lithium hydroxide (16.89 g, 705.44 mmol) is stirred overnight at room temperature. Acetone is concentrated in vacuo. The precipitate is filtered off and the filtrate is extracted with TBME. The aq. layer is adjusted to pH 2.5 by adding 4N hydrochloric acid and immediately extracted with TBME. The organic layer is washed with water, dried over Na₂SO₄ and concentrated in vacuo to a volume of 200 mL. Methyl cyclohexane (500 mL) is added, TBME is concentrated in vacuo and cooled down to −12° C. The precipitate is filtered off, washed with n-heptane and dried in a vacuum oven at 45° C. Yield 87%, m/z 242 [M+H]+

Synthesis of (2S)-2-amino-3-(2-fluoro-4-iodo-phenyl)propanenitrile

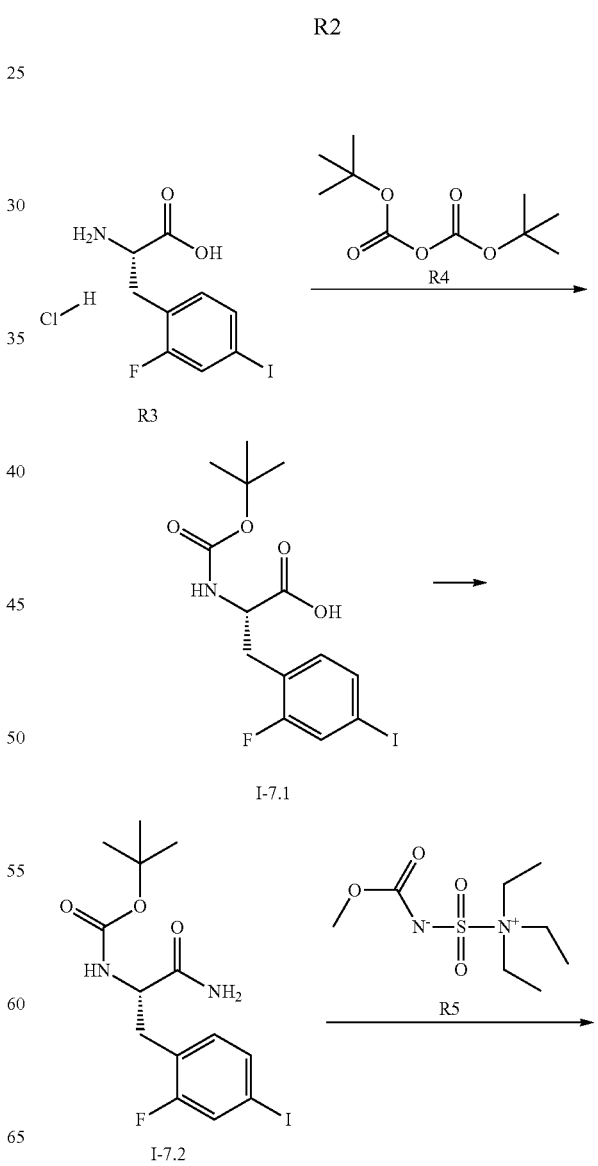

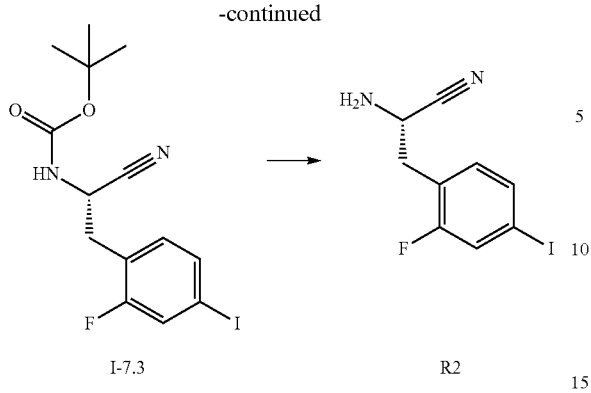

I-7.3    R2

Step 1: Synthesis of I-7.1

To R3 (15.00 g, 43.41 mmol) in dioxane are added R4 (10.42 g, 47.75 mmol) and sodium carbonate solution (2 mol/L, 22.79 mL, 45.58 mmol) and stirred over 2 nights at r.t. R4 (1.90 g, 8.68 mmol) is added and stirred overnight at r.t. The pH value of the reaction mixture is adjusted to 4-5 by adding aq. citric acid solution (10%), afterwards extracted with ethyl acetate. The organic layer is washed with brine, dried and concentrated in vacuo.

Yield 98% m/z 410 [M+H]+, rt 1.21 min, LC-MS Method V012_S01

Step 2: Synthesis of I-7.2

To I-7.1 (23.24 g, 56.80 mmol) in DMF are added N-ethylmorpholine (9.81 g, 85.19 mmol) and TBTU (18.24 g, 56.80 mmol) and stirred 0.5 h at r.t. The reaction mixture is cooled down with an icebath and aq. ammonia (32%, 5.48 g, 102.86 mmol) is added dropwise. The reaction mixture is stirred overnight at r.t., then poured into water (500 mL). The precipitate is filtered off, washed with water and dried in vacuo at 50° C.

Yield 78% m/z 409 [M+H]+, rt 1.05 min, LC-MS Method V011_S01

Step 3: Synthesis of I-7.3

The reaction is carried out under argon atmosphere.

To I-7.2 (14.97 g, 36.67 mmol) in dichloromethane is added a solution of R5 (17.48 g, 73.35 mmol) in dichloromethane and stirred overnight at r.t. The reaction mixture is extracted with water. The organic layer is dried over MgSO4 and concentrated in vacuo. The crude residue is purified by flash chromatography (eluent: cyclohexane/ethyl acetate 1:1).

Yield 79% m/z 391 [M+H]+, rt 1.29 min, LC-MS Method V012_S01

Step 4: Synthesis of R2

To I-7.3 (6.0 g, 15.38 mmol) in acetonitrile (150 mL) is added p-toluenesulfonic acid monohydrate (3.98 g, 20.91 mmol) and stirred at r.t. The precipitate is filtered off, dissolved in ethyl acetate and extracted with sodium hydrogencarbonate solution. The organic layer is concentrated in vacuo, dissolved in ethyl acetate again and extracted with sodium hydrogencarbonate solution. The organic layer is dried over MgSO4 and concentrated in vacuo.

Yield 72% m/z 291 [M+H]+, rt 1.01 min, LC-MS Method V011_S01

Synthesis of 1-(oxetan-3-yl)piperazine (R8)

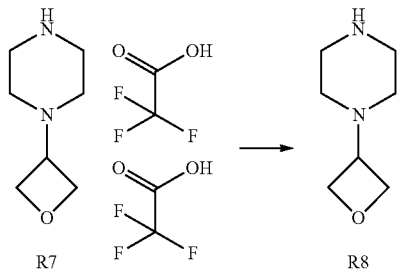

R7    R8

To R7 (500 mg, 1.35 mmol) in diethyl ether is added sodium methanolate (150 mg, 2.78 mmol) and stirred over 2 days at r.t. The precipitate is filtered off and purified by flash chromatography (amino phase, eluent: dichloromethane/methanol 95:5). Yield 86% m/z 143 [M+H]+

Synthesis of 3-(oxetan-3-yl)-3,8-diazabicyclo[3.2.1]octane; 2,2,2-trifluoroacetic acid (R11)

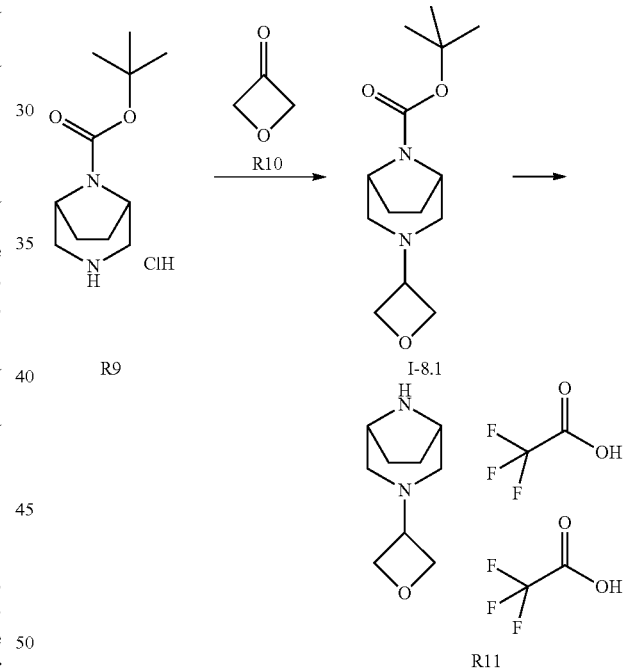

R9    I-8.1

R11

Step 1: Synthesis of I-8.1

The reaction is carried out under nitrogen. To R9 (300 mg, 1.21 mmol) in THF (5 mL) are added R10 (95.60 mg, 1.33 mmol) and sodium acetate (148.40 mg, 1.81 mmol) and stirred for 0.5 h at r.t. Sodium triacetoxy borohydride (349.78 mg, 1.57 mmol) is added and stirred overnight at r.t. The reaction mixture is basified with sodium hydrogencarbonate solution and extracted with ethyl acetate. The organic layer is dried over Na2SO4 and concentrated in vacuo. The crude residue is purified by reversed phase HPLC.

Yield 36% m/z 269 [M+H]+

The following intermediates as shown in Table 12 are synthesized in a similar fashion from the appropriate intermediates:

TABLE 12

| Intermediate | Structure | m/z [M + H]+ | rt (min) | LC-MS method |
|---|---|---|---|---|
| I-8.1.1 | ![structure] | 255 | n.d. | n.d |

Step 2: Synthesis of R11

To I-8.1 (116 mg, 0.43 mmol) in dichloromethane (3 mL) is added trifluoroacetic acid (1.5 mL) and stirred for 1 h at r.t. The reaction mixture is concentrated and crystallized from diethyl ether. Yield 78% m/z 169 [M+H]+, rt 0.20 min, LC-MS Method X011_S03

The following intermediate as shown in Table 13 is synthesized in a similar fashion from the appropriate intermediates:

TABLE 13

| Intermediate | Structure | m/z [M + H]+ | rt (min) | LC-MS method |
|---|---|---|---|---|
| R11.1 | ![structure] | n.d. | n.d. | n.d. |

Synthesis of [1-(oxetan-3-yl)-3,6-dihydro-2H-pyridin-4-yl]trifluoromethanesulfonate (R12)

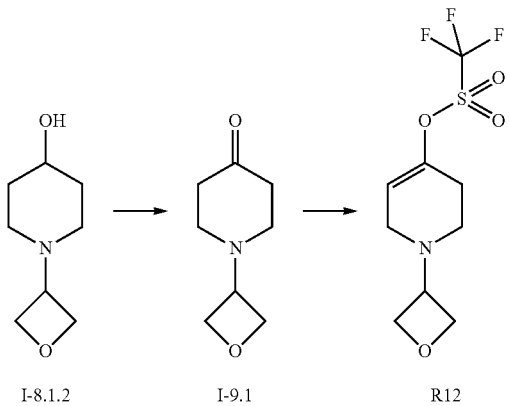

I-8.1.2 → I-9.1 → R12

Step 1: Synthesis of I-9.1

To I-8.1.2 (1.0 g, 6.36 mmol) in dichloromethane (25 mL) is added dess-martin periodinane (3.25 g, 7.66 mmol) and stirred over 2 days at r.t. The precipitate is filtered off and the filtrate is concentrated. The crude residue is purified over ALOX/N (eluent: cyclohexane/ethyl acetate 2:3). Yield 55%.

Step 2: Synthesis of R12

The reaction is carried out under argon atmosphere. I-9.1 (540 mg, 3.48 mmol) is dissolved in THF and cooled down to −78° C. Lithium bis(trimethylsilyl)amide 1 mol/L in THF (4.2 mL, 4.20 mmol) is added dropwise and stirred for further 2 h. N,N-bis(trifluoromethanesulphonyl)aniline (1.37 g, 3.84 mmol) is added and the reaction mixture is allowed to come to r.t. overnight. The reaction mixture is diluted with saturated sodium carbonate solution (10 mL) and extracted with ethyl acetate. The organic layer is washed with saturated sodium carbonate solution and brine. The organic layer is dried and concentrated in vacuo. The crude residue is filtered through an amino phase cartridge (eluent: cyclohexane/ethyl acetate 3:1).

Yield 63% m/z 288 [M+H]+

The following intermediates as shown in Table 14 are synthesized in a similar fashion from the appropriate intermediates:

TABLE 14

| Intermediate | Structure | m/z [M + H]+ | rt (min) | LC-MS method |
|---|---|---|---|---|
| R12.1 | ![structure] | 322 | 1.41 | V011_S01 |

TABLE 14-continued
| Intermediate | Structure | m/z [M + H]+ | rt (min) | LC-MS method |
|---|---|---|---|---|
| R12.2 | 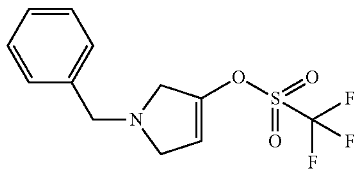 | 308 | 1.38 | V011_S01 |
| R12.3 | mixture of cis isomers | 348 | 1.47 | V011_S01 |
Synthesis of (2S)-2-amino-3-(4-bromo-2-fluoro-phenyl)propanamide hydrochloride (R13)
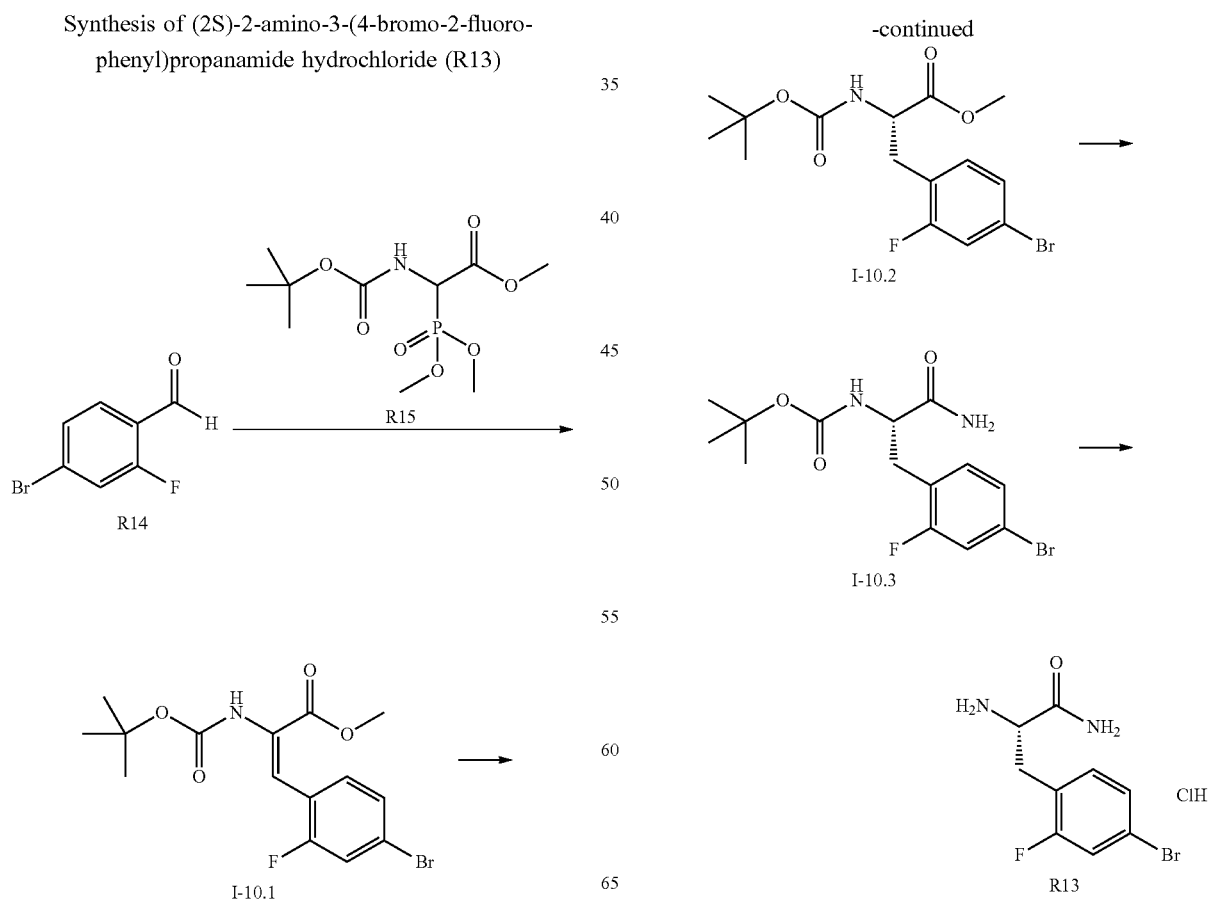

Step 1: Synthesis of I-10.1

The reaction is carried out under nitrogen atmosphere. R15 (48.32 g, 162.56 mmol) is dissolved in methyl-THF (90 mL) and cooled down to −10° C. 1,1,3,3-Tetramethylguanidine (18.72 g, 162.56 mmol) is added dropwise, subsequently rinsed with methyl-THF (15 mL). Afterwards a solution of R14 (30.0 g, 147.78 mmol) in methyl THF (150 mL) is added dropwise at −5° C. and subsequently rinsed with methyl-THF (45 mL). The reaction mixture is stirred 45 minutes at −10° C., then warmed up to 20° C. during ~1.5 h and diluted with water (150 mL) and toluene (150 mL). The organic layer is washed with water and concentrated in vacuo. The crude residue is recrystallized from cyclohexane and dried in a vacuum oven at 50° C.

Yield 87% m/z 374 [M+H]+

Step 2: Synthesis of I-10.2

I-10.1 (45.0 g, 120.26 mmol) in methanol (225 mL) is purged with argon at ~30° C. The oil bath is removed and (+)-1,2-bis((2S,5S)-2,5-diethylphospholano)benzene(cyclooctadiene)Rh(I)triflat (86.9 mg, 0.12 mmol) is added and purged again at 30° C. with argon. The reaction mixture is stirred under hydrogen (40 bar) at 40° C. for 4 h. The reaction mixture is cooled down and filtered over silica gel, subsequently over activated carbon. The filtrate is concentrated in vacuo. The crude residue is dissolved in methanol (225 mL) in a water bath (50° C.). The solution is purged with argon at ~30° C., (+)-1,2-bis((2S,5S)-2,5-diethylphospholano)benzene(cyclooctadiene)Rh(I)triflat (434.50 mg, 0.60 mmol) is added and purged again with argon. The reaction mixture is stirred under hydrogen (40 bar) at 40° C. for ~2 h.

The reaction mixture is cooled down and filtered over activated carbon. The filtrate is concentrated in vacuo.

Yield 92% m/z 376 [M+H]+

Step 3: Synthesis of I-10.3

I-10.2 (41.3 g, 109.78 mmol) is dissolved in methanol (150 mL) at 50° C. Calcium chloride (12.18 g, 109.78 mmol) and ammonia 7N in methanol (122.17 g, 1.1 mol) are added at ~20° C. and stirred for 6 h. Water (250 mL) is added dropwise, the precipitate is filtered off and dried at 50° C.

Yield 88% m/z 361 [M+H]+

Step 4: Synthesis of R13

To I-10.3 (63.2 g, 174.97 mmol) in dichloromethane (550 mL) are added hydrochloric acid in dioxane (4 mol/L, 218.71 mL, 874.85 mmol) dropwise and dichloromethane (150 mL). The reaction mixture is stirred overnight at r.t., diluted with tert. butylmethyl ether (550 mL), stirred for further 3.5 h and the precipitate is filtered off and dried.

Yield >95% m/z 261 [M+H]+

Synthesis of benzyl 2,3,3a,4,6,6a-hexahydro-1H-pyrrolo[3,4-c]pyrrole-5-carboxylate (R16)

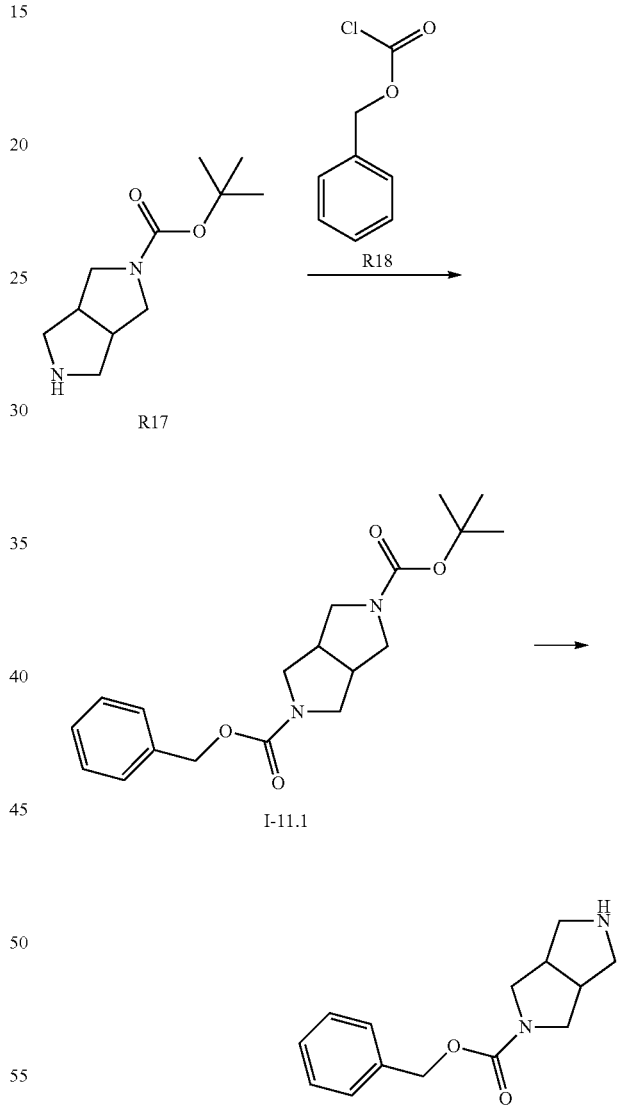

Step 1: Synthesis of I-11.1

R17 (4.5 g, 21.20 mmol) in dichloromethane (100 mL) and TEA (3.55 mL, 25.44 mmol) is cooled down to 0° C. and a solution of R18 (3.78 mL, 25.44 mmol) in dichloromethane (5 mL) is added dropwise. The reaction mixture is allowed to come to r.t. and stirred for further 1 h. The reaction mixture is diluted with dichloromethane and potassium carbonate solution (5%). The organic layer is dried and concentrated in vacuo. The crude residue is purified by reversed phase HPLC.

Yield 85% m/z 347 [M+H]+, rt 0.74 min, LC-MS Method X018_S02

Step 2: Synthesis of R16

To I-11.1 (6.05 g, 17.46 mmol) in dioxane (60 mL) is added hydrochloric acid in dioxane (4 mol/L, 17.46 mL, 69.86 mmol) and stirred 18 h at r.t. The reaction mixture is basified with sodium hydrogencarbonate solution and extracted with ethyl acetate. The aq. layer is extracted with a mixture of dichloromethane/isopropanol 9:1. The combined organic layers are dried over $MgSO_4$ and concentrated in vacuo.

Yield 100% m/z 247 [M+H]+, rt 0.35 min, LC-MS Method X018_S02

Synthesis of R19

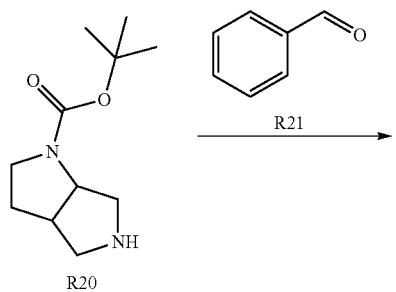

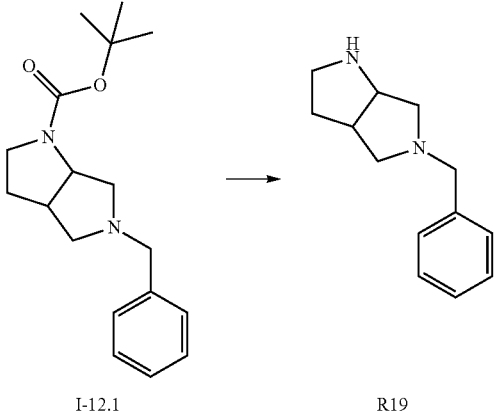

Step 1: Synthesis of I-12.1

To R20 (6.0 g, 28.26 mmol) in dichloromethane (200 mL) are added R21 (3.16 mL, 31.09 mmol) and acetic acid (1.62 mL, 28.26 mmol) and stirred for 1 h at r.t. Sodium triacetoxyborohydride (9.46 g, 42.40 mmol) is added and stirred overnight at r.t. The reaction mixture is diluted with dichloromethane and saturated sodium hydrogencarbonate solution. The organic layer is dried and concentrated in vacuo.

Yield 100% m/z 303 [M+H]+, rt 1.34 min, LC-MS Method V011_501.

The following intermediates as shown in Table 15 are synthesized in a similar fashion from the appropriate intermediates:

TABLE 15

| Intermediate | Structure | m/z [M + H]+ | rt (min) | LC-MS method |
|---|---|---|---|---|
| I-12.1.1 | mixture of trans isomers | 303 | 1.26 | V011_S01 |
| I-12.1.2 | mixture of cis isomers | 303 | 1.38 | V011_S01 |

Step 2: Synthesis of R19

To I-12.1 (8.4 g, 27.78 mmol) in dioxane (150 mL) is added hydrochloric acid in dioxane (4 mol/L, 27.78 mL, 111.11 mmol) and stirred overnight at r.t. The reaction mixture is concentrated in vacuo and triturated with diethyl ether. The precipitate is filtered off, dissolved in aq. ammonia (25%) and extracted with dichloromethane and a mixture of dichlorormethane/isopropanol 9:1. The combined organic layers are dried over $MgSO_4$ and concentrated in vacuo.

Yield 88% m/z 203 [M+H]+, rt 0.89 min, LC-MS Method V011_S01.

The following intermediates as shown in Table 16 are synthesized in a similar fashion from the appropriate intermediates:

TABLE 16

| Intermediate | Structure | m/z [M + H]+ | rt (min) | LC-MS method |
|---|---|---|---|---|
| R19.1 | mixture of trans isomers | 203 | 0.82 | V011_S01 |
| R19.2 | mixture of cis isomers | 203 | 0.90 | V011_S01 |

Synthesis of 2-benzyl-1,3,3a,4,6,6a-hexahydrocyclopenta[c]pyrrol-5-one (R22)

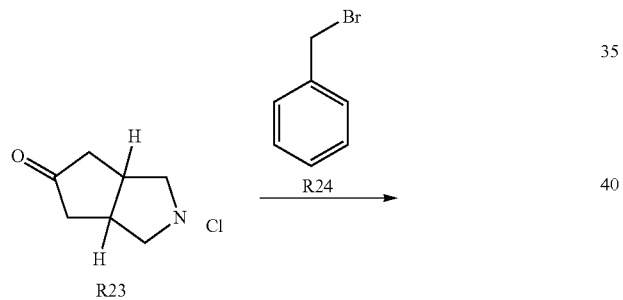

To R23, mixture of cis isomers, (3.5 g, 21.66 mmol) in DMF (40 mL) are added DIPEA (11.18 mL, 65.00 mmol) and R24 (2.83 mL, 23.82 mmol) and stirred overnight at r.t. The precipitate is filtered off and the mother liquor is purified by reversed phase HPLC.

Yield 36% m/z 216 [M+H]+, rt 1.02 min, LC-MS Method V011_S01.

EXAMPLES (rt=retention time) Deprotection Methods: TSA (toluene sulfonic acid cf. Example 1). Stereochemistry at the carbon atom adjacent to the nitrile group is assigned: Stereo bond means S-isomer, non-stereo bond means 1:1 mixture of stereoisomers.

TABLE 17

| Example | Structure | Educt | Syn./Deprot. Method | Yield [%] |
|---|---|---|---|---|
| 1 | 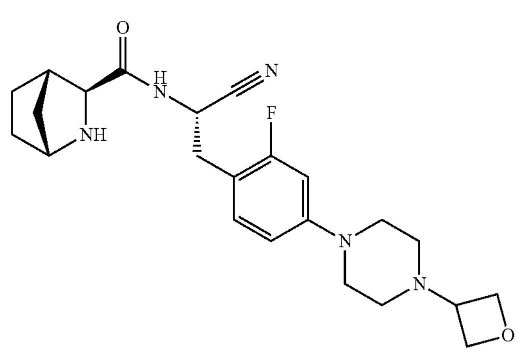 [SMILES: N#C[C@H](Cc1ccc(N2CCN(C3COC3)CC2)cc1F)NC(=O)[C@H]1N[C@@H]2CC[C@H]1C2] | I-1.3 | A/TSA | 69 |

TABLE 17-continued
| Example | Structure | Educt | Syn./Deprot. Method | Yield [%] |
|---|---|---|---|---|
| 2 | 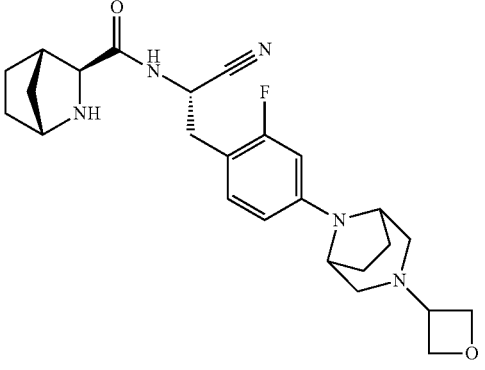 [SMILES: N#C[C@H](Cc1ccc(N2C3CCC2CN(C2COC2)C3)cc1F)NC(=O)[C@H]1N[C@@H]2CC[C@H]1C2] | I-1.3.1 | A/TSA | 77 |
| 3 | 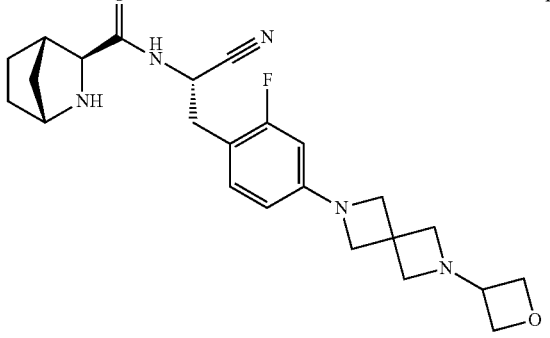 | I-1.3.2 | A/TSA | 18 |
| 4 | 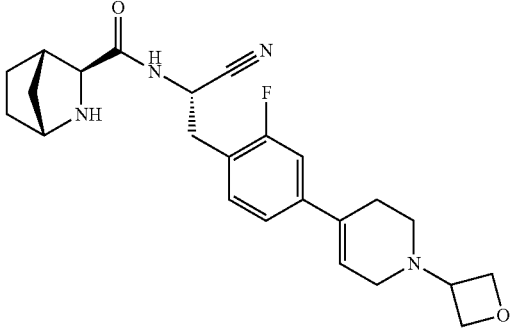 [SMILES: N#C[C@H](Cc1ccc(C2=CCN(C3COC3)CC2)cc1F)NC(=O)[C@H]1N[C@@H]2CC[C@H]1C2] | I-2.1 | A1/TSA | 95 |
| 5 | 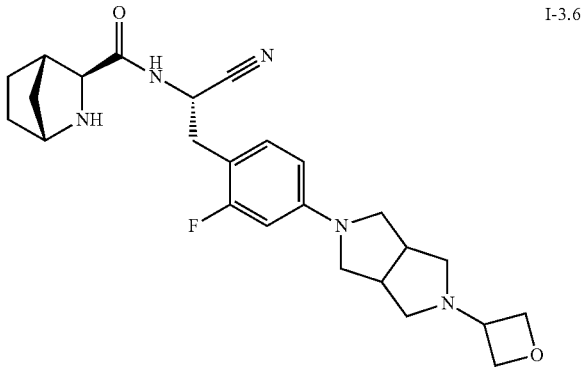 | I-3.6 | B/TSA | 48 |

TABLE 17-continued

| Example | Structure | Educt | Syn./Deprot. Method | Yield [%] |
|---|---|---|---|---|
| 6 | 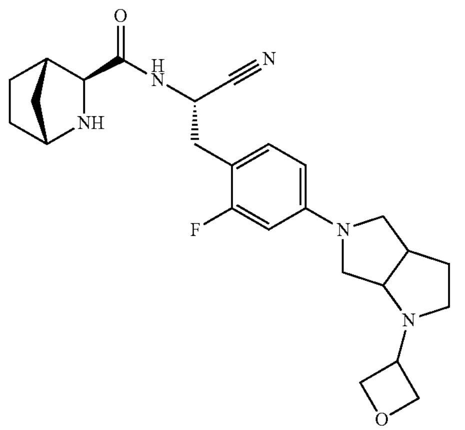 [SMILES: N#C[C@H](Cc1ccc(N2CC3CCN(C4COC4)C3C2)cc1F)NC(=O)[C@H]1N[C@@H]2CC[C@H]1C2] | I-3.6.1 | B/TSA | 70 |
| 7 | 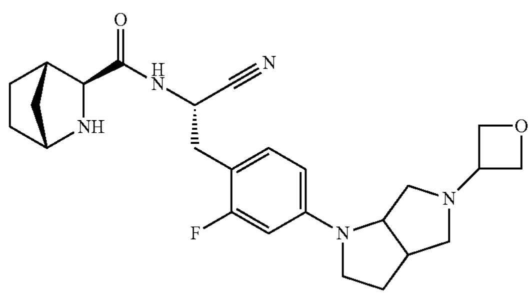 [SMILES: N#C[C@H](Cc1ccc(N2CCC3CN(C4COC4)CC32)cc1F)NC(=O)[C@H]1N[C@@H]2CC[C@H]1C2] | I-3.6.2 | B/TSA | 72 |
| 8 | mixture of trans isomers | I-3.6.3 | B/TSA | 64 |
| 9 | mixture of cis isomers | I-3.6.4 | B/TSA | 64 |

TABLE 17-continued

| Example | Structure | Educt | Syn./Deprot. Method | Yield [%] |
|---|---|---|---|---|
| 10 | 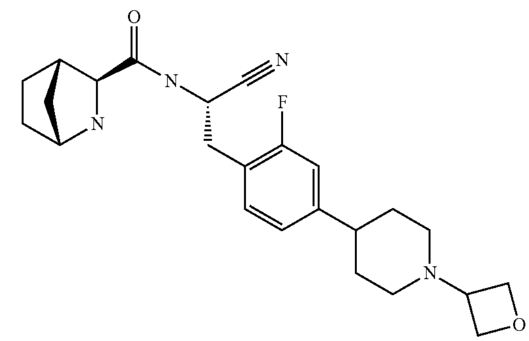 [SMILES: N#C[C@H](Cc1ccc(C2CCN(C3COC3)CC2)cc1F)NC(=O)[C@H]1N[C@@H]2CC[C@H]1C2] | I-4.3 | B1/TSA | 77 |
| 11 | 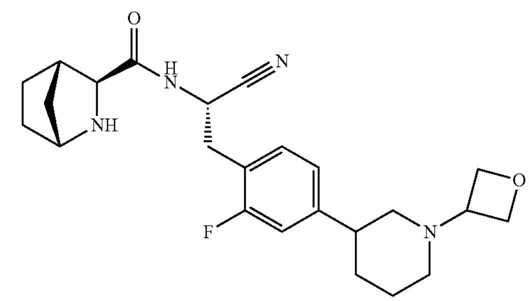 [SMILES: N#C[C@H](Cc1ccc(C2CCCN(C3COC3)C2)cc1F)NC(=O)[C@H]1N[C@@H]2CC[C@H]1C2] | I-4.3.1 | B2/TSA | 68 |
| 12 | 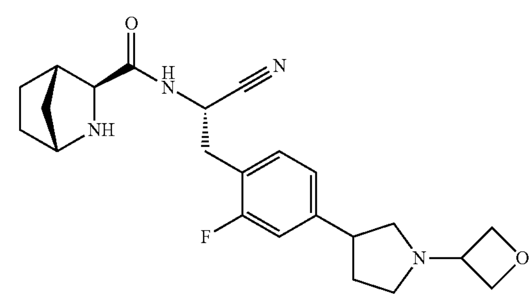 [SMILES: N#C[C@H](Cc1ccc(C2CCN(C3COC3)C2)cc1F)NC(=O)[C@H]1N[C@@H]2CC[C@H]1C2] | I-4.3.2 | B2/TSA | 70 |
| 13 | | I-4.3.3 | B2/TSA | 89 | mixture of cis isomers

TABLE 17-continued

| Example | Structure | Educt | Syn./Deprot. Method | Yield [%] |
|---|---|---|---|---|
| 14 | (structure shown) mixture of cis isomers | I-4.3.4 | B2/TSA | 76 |
| 15. | (structure shown) | I-5.5.1 | C/TSA | 64 |
| 16. | (structure shown) | I-5.5.2 | PPA | 46 |

Analytical Data of Examples

TABLE 18

| Ex. | m/z [M + H]+ | rt [min] | LC-MS-Method |
|---|---|---|---|
| 1 | 428 | 0.60 | 004_CA05 |
| 2 | 454 | 0.80 | X011_S03 |
| 3 | 440 | 0.50 | X011_S03 |
| 4 | 425 | 0.58 | X011_S03 |
| 5 | 454 | 0.76 | 003_CA04 |
| 6 | 454 | 1.05 | V011_S01 |
| 7 | 454 | 0.77 | 003_CA04 |
| 8 | 454 | 0.72 | 003_CA04 |
| 9 | 454 | 0.75 | 003_CA04 |

TABLE 18-continued

| Ex. | m/z [M + H]+ | rt [min] | LC-MS-Method |
|---|---|---|---|
| 10 | 427 | 0.61 | X011_S03 |
| 11 | 427 | 0.68 | 004_CA05 |
| 12 | 413 | 0.71 | 003_CA04 |
| 13 | 453 | 1.06 | V011_S01 |
| 14 | 453 | 1.13 | V011_S01 |
| 15 | 442 | 0.51 | X011_S03 |
| 16 | 468 | 1.03 | V011_S01 |

TABLE 19

List of abbreviations

| | |
|---|---|
| ACN | acetonitrile |
| aq. | aqueous |
| BOC | tert. butyloxycarbonyle- |
| d | day |
| DCM | dichloromethane |
| DEA | diethylamine |
| DIPEA | n,n-diisopropylethylamine |
| DIPE | diisopropyl ether |
| DMAP | 4-dimethylaminopyridine |
| DMF | n,n-dimethylformamide |
| DMSO | dimethyl sulfoxide |
| EA | ethyl acetate |
| FA | formic acid |
| h | hour |
| HATU | o-(7-azabenzotriazol-1-yl)-N,N,N',N'-tetramethyluronium hexafluoro-phosphate |
| LiOH | lithium hydroxide |
| MeOH | methanol |
| MeTHF | methyl tetrahydrofuran |
| NaH | sodium hydride |
| PE | petrol ether |
| RT, r.t. | room temperature, e.g. 15-25° C. |
| rt | retention time |
| TBME | tert-butyl methyl ether |
| TBTU | o-(1H-benzo-1,2,3-triazol-1-yl)-N,N,N',N'-tetramethyluronium tetrafluoroborate |
| TEA | triethylamine |
| TFA | trifluoroacetic acid |
| THF | tetrahydrofuran |
| TSA | toluene sulfonic acid |

Pharmacological Data

Other features and advantages of the present invention will become apparent from the following more detailed examples which illustrate, by way of example, the principles of the invention.

Inhibition of Human DPPI (Cathepsin C)

Materials: Microtiterplates (Optiplate-384 F) were purchased from PerkinElmer (Prod.No. 10 6007270). The substrate Gly-Arg-AMC was from Biotrend (Prod.-No. 808756 Custom peptide).

Bovine serum albumin (BSA; Prod.No. A3059) and Dithiothreitol (DTT; Prod.No D0632) were from Sigma. TagZyme buffer was from Riedel-de-Haen (Prod.-No. 04269), NaCl was from Merck (Prod.-No. 1.06404.1000) and morpholinoethane sulfonic acid (MES), was from Serva (Prod.-No. 29834). The DPP1 inhibitor Gly-Phe-DMK was purchased from MP Biomedicals 15 (Prod.-No. 03DK00625). The recombinant human DPPI was purchased from Prozymex. All other materials were of highest grade commercially available.

The following buffers were used: MES buffer: 25 mM MES, 50 mM NaCl, 5 mM DTT, adjusted to pH 6.0, containing 0.1% BSA; TAGZyme Buffer: 20 mM NaH2PO4, 150 mM NaCl adjusted to pH 20 6.0 with HCl Assay conditions: The recombinant human DPPI was diluted in TAGZyme buffer to 1 U/ml (38.1 µg/ml, respectively), and then activated by mixing in a 1:2 ratio with a Cysteamine aqueous solution (2 mM) and incubating for 5 min at room temperature.

Five uL test compound (final concentration 0.1 nM to 100 µM) in aqua bidest 5 (containing 4% DMSO, final DMSO concentration 1%) were mixed with 10 µL of DPPI in MES buffer (final concentration 0.0125 ng/µL) and incubated for 10 min. Then, 5 µL of substrate in MES buffer (final concentration 50 µM) were added. The microtiter plates were then incubated at room temperature for 30 min. Then, the reaction was stopped by adding 10 µL of Gly-Phe-DMK in 10 MES-buffer (final concentration 1 µM). The fluorescence in the wells was determined using a Molecular Devices SpectraMax M5 Fluorescence Reader (Ex 360 nm, Em 460 nm) or an Envision Fluorescence Reader (Ex 355 nm, Em 460 nm).

Each assay microtiter plate contained wells with vehicle controls (1% DMSO in bidest+0.075% 15 BSA) as reference for non-inhibited enzyme activity (100% Ctl; high values) and wells with inhibitor (Gly-Phe-DMK, in bidest+1% DMSO+0.075% BSA, final concentration 1 µM) as controls for background fluorescence (0% Ctl; low values).

The analysis of the data was performed by calculating the percentage of fluorescence in the presence of test compound in comparison to the fluorescence of the vehicle control after 20 subtracting the background fluorescence using the following formula:

$$(RFU(\text{sample}) - RFU(\text{background})) * 100 / (RFU(\text{control}) - RFU(\text{background}))$$

Data from these calculations were used to generate IC50 values for inhibition of DPPI, respectively.

| Example | Inhibition of DPPI IC50 [µM] |
|---|---|
| 1 | 0.0117 |
| 2 | 0.0144 |
| 3 | 0.0216 |
| 4 | 0.0056 |
| 5 | 0.0165 |
| 6 | 0.0135 |
| 7 | 0.0099 |
| 8 | 0.0355 |
| 9 | 0.0176 |
| 10 | 0.0601 |
| 11 | 0.0527 |
| 12 | 0.0294 |
| 13 | 0.0797 |
| 14 | 0.0293 |
| 15 | 0.0665 |
| 16 | 0.0754 |

Combinations

The compounds of general formula I may be used on their own or combined with other active substances of formula I according to the invention. The compounds of general formula I may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-□B signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, Non-steroidal anti-inflammatory agents (NSAIDs), CRTH2 antagonists, DP1-receptor modulators, Thromboxane receptor antagonists, CCR3 antagonists, CCR$^4$ antagonists, CCR1 antagonists, CCR5 antagonists, CCR6 antagonists, CCR7 antagonists, CCR8 antagonists, CCR9 antagonists, CCR30 antagonists, CXCR$^3$ antagonists, CXCR$^4$ antagonists, CXCR$^2$ antagonists, CXCR$^1$ antagonists, CXCR5 antagonists, CXCR6 antagonists, CX3CR$^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Matriptase-inhibitors, Melanocortin receptor (MC1R, MC2R, MC3R, MC4R, MC5R) modulators, CGRP antagonists, Endothelin antagonists, TNF□ antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, NE-inhibitors, MMP9 inhibitors, MMP12 inhibitors, but also combinations of two or three active substances.

Preferred are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, NE-inhibitors, MMP9 inhibitors, MMP12 inhibitors, but also combinations of two or three active substances, i.e.:

Betamimetics with corticosteroids, PDE4-inhibitors, CRTH2-inhibitors or LTD4-antagonists, Anticholinergics with betamimetics, corticosteroids, PDE4-inhibitors, CRTH2-inhibitors or LTD4-antagonists, Corticosteroids with PDE4-inhibitors, CRTH2-inhibitors or LTD4-antagonists PDE4-inhibitors with CRTH2-inhibitors or LTD4-antagonists CRTH2-inhibitors with LTD4-antagonists.

INDICATIONS

The compounds of the invention and their pharmaceutically acceptable salts have activity as pharmaceuticals, in particular as inhibitors of dipeptidyl peptidase I activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency, bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, polyangiitis (Wegener Granulomatosis) and pulmonary hypertension; anti-tussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, Candida, aspergillus, cryptococcal meningitis, Pneumocystis carnii, cryptosporidiosis, histoplasmosis, toxoplasmosis, trypanosome infection and leishmaniasis.

9. pain: Recent literature data from Cathepsin C-deficient mice point to a modulatory role of Cathepsin C in pain sensation. Accordingly, inhibitors of Cathepsin C may also be useful in the clinical setting of various form of chronic pain, e.g. inflammatory or neuropathic pain.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What we claim:

1. A compound of formula I

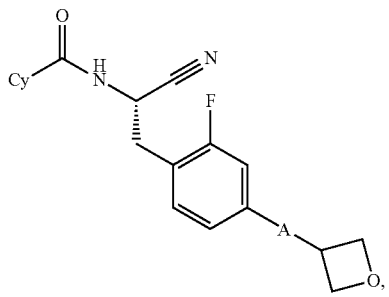

wherein
Cy denotes a group of formula $Cy^1$ or $Cy^2$,

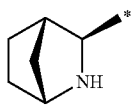

$Cy^1$

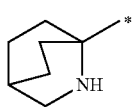

$Cy^2$

A denotes a 5 to 10 membered monocyclic, bicyclic or spirocyclic heterocycle containing 1 or 2 N-atoms, or a salt thereof.

2. A compound of formula I according to claim 1, wherein A denotes a group of formula (a) or (b),

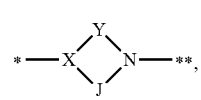

(a)

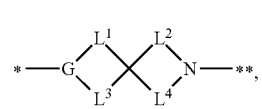

(b)

X is selected from among N, —CH— and =C—
Y is selected from among —(CH$_2$)$_m$— or =CH—(CH$_2$)$_n$—
J denotes —(CH$_2$)$_o$—
Y and J are optionally linked by a bond or —(CH$_2$)$_p$—
m, n, o independently from each other denote 1, 2, 3 or 4,
p denotes 1 or 2,
G denotes N or —CH—
$L^1$, $L^2$, $L^3$, $L^4$ independently from each other denote —CH$_2$— or —CH$_2$—CH$_2$—
or a salt thereof.

3. A compound of formula I according to claim 1, wherein A denotes a group of formula (a.I)

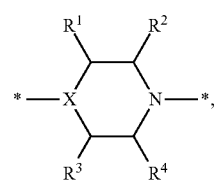

(a.I)

X denotes N or —CH—
$R^1$, $R^2$, $R^3$, $R^4$ independently from each other denote H or optionally one pair selected from among $R^1$ and $R^3$, $R^1$ and $R^4$, $R^2$ and $R^3$ and $R^2$ and $R^4$ together denotes (—CH$_2$—) or —CH$_2$—CH$_2$—.
or a salt thereof.

4. A compound of formula I according to claim 1, wherein A denotes a group of formula (a.II)

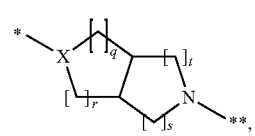

(a.II)

X denotes N or —CH—
q, s independently from each other denote 0, 1 or 2
t, r independently from each other denote 1 or 2,
or a salt thereof.

5. A compound of formula I according to claim 1, wherein A denotes a group of formula (b.I),

(b.I)

to G denotes N or —CH— or a salt thereof.

6. A compound of formula I according to claim 1, wherein A denotes a group selected from among formulas (1) to (12)

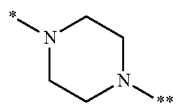 (1)

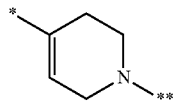 (2)

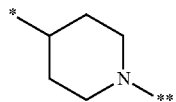 (3)

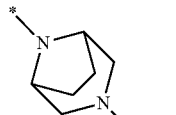 (4)

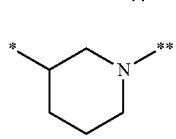 (5)

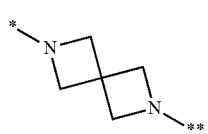 (6)

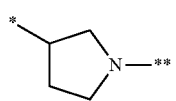 (7)

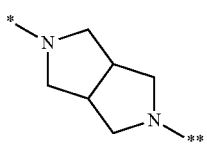 (8)

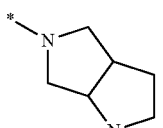 (9)

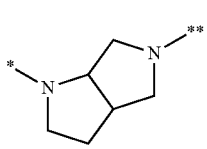 (10)

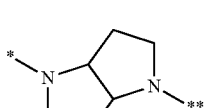 (11)

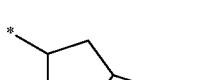 (12)

or a salt thereof.

7. A pharmaceutical composition comprising one or more compounds of formula I according to claim 1 or a pharmaceutically active salt thereof.

8. A pharmaceutical composition comprising a compound of formula I, according to claim 1 or a pharmaceutically acceptable salt thereof, and a pharmaceutically active compound selected from the group consisting of betamimetics, anticholinergics, corticosteroids, PDE4-inhibitors, LTD4-antagonists, EGFR-inhibitors, CRTH2 inhibitors, 5-LO-inhibitors, Histamine receptor antagonists, CCR9 antagonists and SYK-inhibitors, NE-inhibitors, MMP9 inhibitors, MMP12 inhibitors, and combinations thereof.

* * * * *